(12) United States Patent
Horikoshi et al.

(10) Patent No.: US 6,905,852 B1
(45) Date of Patent: Jun. 14, 2005

(54) **HERBICIDE-RESISTANT PROTOPORPHYRINOGEN OXIDASE ISOLATED FROM *NICOTIANA TABACUM***

(75) Inventors: Mamoru Horikoshi, Osaka (JP); Koki Mametsuka, Osaka (JP); Takashi Hirooka, Osaka (JP)

(73) Assignee: Nihon Nohyaku Co., Ltd., Tokyo (JP)

( * ) Notice: Subject to any disclaimer, the term of this patent is extended or adjusted under 35 U.S.C. 154(b) by 0 days.

(21) Appl. No.: 09/508,418

(22) PCT Filed: Sep. 10, 1998

(86) PCT No.: PCT/JP98/04064

§ 371 (c)(1),
(2), (4) Date: Jun. 8, 2000

(87) PCT Pub. No.: WO99/13087

PCT Pub. Date: Mar. 18, 1999

(30) Foreign Application Priority Data

Sep. 11, 1997 (JP) .............................. 9-265084

(51) Int. Cl.[7] .............................. C12N 9/02
(52) U.S. Cl. .................................. 435/189
(58) Field of Search ......................... 435/189

(56) References Cited

U.S. PATENT DOCUMENTS 5,939,602 A * 8/1999 Volrath et al. .............. 800/300

FOREIGN PATENT DOCUMENTS

WO            95/34659 A     12/1995
WO       WO 97/32011    *    9/1997

OTHER PUBLICATIONS

Ichinose et al. (1995) J Plant Physiol 146:693–698.*
Branden et al. "Introduction to Protein Structure", p. 247, Garland Publishing Inc., New York, 1991.*
Williams et al. (1998) Biochemistry 37:7096–7102.*
Witkowski et al. (1999) Biochemistry 38:11643–11650.*
Proc. Natl. Acad.Sci., vol. 94, No. 16, (1997), Inna Lermontova et al. "Cloning and characterization of a plastidal and a mitochondrial isoform of tobacco protoporphyrinogen IX oxidase" p. 8895–8900 (Copy submitted to USPTO by WIPO).
Biochem.J., vol. 260, (1989), Michel Matringe et al. "Protoporphyrinogen oxidase as a molecular target for diphenyl ehter herbicides" p. 231–235 (Copy submitted to USPTO by WIPO).
The Journal of Biological Chemistry, vol. 270, No. 14, (1995), Koichi Nishimura et al. "CLoning of a Human cDNA for Protoporphyrinogen Oxidase by Complementation in Vivo of a hemG Mutuant of *Escherichia coli*" p. 8076–8080 (Copy submitted to USPTO by WIPO).
Journal of General Microbiology, vol. 113, (1979), A.Sasarman,P. et al "Mapping of a New hem Gene in *Escherichia coli* K12" p. 297–303 (Copy submitted to USPTO by WIPO).
Gene, vol. 182, No. 1–2, (1996), Shin–ichiro Narita et al. "Molecular cloning and characterization of a cDNA that encodes protoporphyrinogen oxidase of *Arabidopsis thaliana*" p. 169–175 (Copy submitted to USPTO by WIPO).

* cited by examiner

*Primary Examiner*—David J. Steadman
(74) *Attorney, Agent, or Firm*—Sughrue Mion, PLLC

(57) ABSTRACT

A protoporphyrinogen oxidase tolerant to photobleaching herbicide and derivatives thereof, comprising a polypeptide having the amino acid sequence represented by SEQ ID No. 2 or mutated peptides derived therefrom by deletion, addition, substitution, etc. of one or more amino acids in the above amino acid sequence and having an activity substantially equivalent to that of the protoporphyrinogen oxidase. The acquisition of the novel protoporphyrinogen oxidase, which is highly tolerant to photobleaching herbicide and originates in plant, make it possible to construct plants highly tolerant to photobleaching herbicide via the expression of this enzyme in host plants.

1 Claim, 2 Drawing Sheets

SEQUENCE LISTING

```
<160> NUMBER OF SEQ ID NOS: 11

<210> SEQ ID NO 1
<211> LENGTH: 1874
<212> TYPE: DNA
<213> ORGANISM: Nicotiana tabacum
<220> FEATURE:
<221> NAME/KEY: exon
<222> LOCATION: (26)..(1672)
<221> NAME/KEY: misc_feature
<223> OTHER INFORMATION: Strain name: Xanthi NC

<400> SEQUENCE: 1
agcgcggtct acaagtcagg cagtc atg aca aca act ccc atc gcc aat cat        52
                            Met Thr Thr Thr Pro Ile Ala Asn His
                             1               5 cct aat att ttc act cac cag tcg tcg tca tcg cca ttg gca ttc tta       100
Pro Asn Ile Phe Thr His Gln Ser Ser Ser Ser Pro Leu Ala Phe Leu
 10                  15                  20                  25 aac cgt acg agt ttc atc cct ttc tct tca atc tcc aag cgc aat agt       148
Asn Arg Thr Ser Phe Ile Pro Phe Ser Ser Ile Ser Lys Arg Asn Ser
                     30                  35                  40 gtc aat tgc aat ggc tgg aga aca cga tgc tcc gtt gcc aaa gat tac       196
Val Asn Cys Asn Gly Trp Arg Thr Arg Cys Ser Val Ala Lys Asp Tyr
             45                  50                  55 aca gtt cct tcc tca gcg gtc gac ggc gga ccc gcc gcg gag ctg gac       244
```

```
Thr Val Pro Ser Ser Ala Val Asp Gly Gly Pro Ala Ala Glu Leu Asp
        60                  65                  70 tgt gtt ata gtt gga gca gga att agt ggc ctc tgc att gcg cag gtg    292
Cys Val Ile Val Gly Ala Gly Ile Ser Gly Leu Cys Ile Ala Gln Val
 75                  80                  85 atg tcc gct aat tac ccc aat ttg atg gta acc gag gcg aga gat cgt    340
Met Ser Ala Asn Tyr Pro Asn Leu Met Val Thr Glu Ala Arg Asp Arg
 90                  95                 100                 105 gcc ggt ggc aac ata acg act gtg gaa aga gac ggc tat ttg tgg gaa    388
Ala Gly Gly Asn Ile Thr Thr Val Glu Arg Asp Gly Tyr Leu Trp Glu
                110                 115                 120 gaa ggt ccc aac agt ttc cag ccg tcc gat cct atg ttg act atg gca    436
Glu Gly Pro Asn Ser Phe Gln Pro Ser Asp Pro Met Leu Thr Met Ala
                125                 130                 135 gta gat tgt gga ttg aag gat gat ttg gtg ttg gga gat cct aat gcg    484
Val Asp Cys Gly Leu Lys Asp Asp Leu Val Leu Gly Asp Pro Asn Ala
        140                 145                 150 ccc cgt ttc gtt ttg tgg aag ggt aaa tta agg ccc gtc ccc tca aaa    532
Pro Arg Phe Val Leu Trp Lys Gly Lys Leu Arg Pro Val Pro Ser Lys
        155                 160                 165 ctc act gat ctt ccc ttt ttt gat ttg atg agc att cct ggc aag ttg    580
Leu Thr Asp Leu Pro Phe Phe Asp Leu Met Ser Ile Pro Gly Lys Leu
170                 175                 180                 185 aga gct ggt ttt ggt ccc att ggc ctc cgc cct tca cct cca ggt cat    628
Arg Ala Gly Phe Gly Pro Ile Gly Leu Arg Pro Ser Pro Pro Gly His
                190                 195                 200 gag gaa tca gtt gag cag ttc gtg cgt cgt aat ctt ggt ggc gaa gtc    676
Glu Glu Ser Val Glu Gln Phe Val Arg Arg Asn Leu Gly Gly Glu Val
                205                 210                 215 ttt gaa cgc ttg ata gaa cca ttt tgt tct ggt gtt tat gct ggt gat    724
Phe Glu Arg Leu Ile Glu Pro Phe Cys Ser Gly Val Tyr Ala Gly Asp
                220                 225                 230 ccc tca aaa ctg agt atg aaa gca gca ttt ggg aaa gtt tgg aag ttg    772
Pro Ser Lys Leu Ser Met Lys Ala Ala Phe Gly Lys Val Trp Lys Leu
        235                 240                 245 gaa gaa act ggt ggt agc att att gga gga acc ttt aaa gca ata aag    820
Glu Glu Thr Gly Gly Ser Ile Ile Gly Gly Thr Phe Lys Ala Ile Lys
250                 255                 260                 265 gag aga tcc agt aca cct aaa gcg ccc cgc gat ccg cgt tta cct aaa    868
Glu Arg Ser Ser Thr Pro Lys Ala Pro Arg Asp Pro Arg Leu Pro Lys
                270                 275                 280 cca aaa gga cag aca gtt gga tca ttc agg aag ggt ctc aga atg ctg    916
Pro Lys Gly Gln Thr Val Gly Ser Phe Arg Lys Gly Leu Arg Met Leu
        285                 290                 295 ccg gat gca atc agt gca aga ttg gga agc aaa tta aaa cta tca tgg    964
Pro Asp Ala Ile Ser Ala Arg Leu Gly Ser Lys Leu Lys Leu Ser Trp
        300                 305                 310 aag ctt tct agc att act aag tca gaa aaa gga gga tat cac ttg aca    1012
Lys Leu Ser Ser Ile Thr Lys Ser Glu Lys Gly Gly Tyr His Leu Thr
        315                 320                 325 tac gag aca cca gaa gga gta gtt tct ctt caa agt cga agc att gtc    1060
Tyr Glu Thr Pro Glu Gly Val Val Ser Leu Gln Ser Arg Ser Ile Val
330                 335                 340                 345 atg act gtg cca tcc tat gta gca agc aac ata tta cgt cct ctt tcg    1108
Met Thr Val Pro Ser Tyr Val Ala Ser Asn Ile Leu Arg Pro Leu Ser
                350                 355                 360 gtt gcc gca gca gat gca ctt tca aat ttc tac tat ccc cca gtt gga    1156
Val Ala Ala Ala Asp Ala Leu Ser Asn Phe Tyr Tyr Pro Pro Val Gly
        365                 370                 375
```

```
gca gtc aca att tca tat cct caa gaa gct att cgt gat gag cgt ctg      1204
Ala Val Thr Ile Ser Tyr Pro Gln Glu Ala Ile Arg Asp Glu Arg Leu
        380                 385                 390 gtt gat ggt gaa cta aag gga ttt ggg cag ttg cat cca cgt aca cag      1252
Val Asp Gly Glu Leu Lys Gly Phe Gly Gln Leu His Pro Arg Thr Gln
395                 400                 405 gga gtg gaa aca cta gga acg ata tat agt tca tca ctc ttc cct aac      1300
Gly Val Glu Thr Leu Gly Thr Ile Tyr Ser Ser Ser Leu Phe Pro Asn
410                 415                 420                 425 cgt gcc cca aaa ggt cgg gta cta ctc ttg aac tac att gga gga gca      1348
Arg Ala Pro Lys Gly Arg Val Leu Leu Leu Asn Tyr Ile Gly Gly Ala
                430                 435                 440 aaa aat cct gaa att ttg tct aag acg gag agc caa ctt gtg gaa gta      1396
Lys Asn Pro Glu Ile Leu Ser Lys Thr Glu Ser Gln Leu Val Glu Val
        445                 450                 455 gtt gat cgt gac ctc aga aaa atg ctt ata aaa ccc aaa gct caa gat      1444
Val Asp Arg Asp Leu Arg Lys Met Leu Ile Lys Pro Lys Ala Gln Asp
460                 465                 470 cct ctt gtt gtg ggt gtg cga gta tgg cca caa gct atc cca cag ttt      1492
Pro Leu Val Val Gly Val Arg Val Trp Pro Gln Ala Ile Pro Gln Phe
475                 480                 485 ttg gtt ggt cat ctg gat acg cta agt act gca aaa gct gct atg aat      1540
Leu Val Gly His Leu Asp Thr Leu Ser Thr Ala Lys Ala Ala Met Asn
490                 495                 500                 505 gat aat ggg ctt gaa ggg ctg ttt ctt ggg ggt aat tat gtg tca ggt      1588
Asp Asn Gly Leu Glu Gly Leu Phe Leu Gly Gly Asn Tyr Val Ser Gly
                510                 515                 520 gta gca ttg ggg agg tgt gtt gaa ggt gct tat gaa gtt gca tcc gag      1636
Val Ala Leu Gly Arg Cys Val Glu Gly Ala Tyr Glu Val Ala Ser Glu
        525                 530                 535 gta aca gga ttt ctg tct cgg tat gca tac aaa tga aacctgtgtt          1682
Val Thr Gly Phe Leu Ser Arg Tyr Ala Tyr Lys
540                 545 gggggtagtc caaaccttgt tagtagtacg atcatgcctt gggaaaattg gcatgtgcct   1742
aaaagttttg ctcattagag ttattttagc cttggtaaat gatttgtact tgatatcagt   1802
cgttttcttt gagataaaat gttcctgttc aggaaatata atgtatatca attttaaaca   1862
aaaaaaaaaa aa                                                       1874

<210> SEQ ID NO 2
<211> LENGTH: 548
<212> TYPE: PRT
<213> ORGANISM: Nicotiana tabacum
<220> FEATURE:
<221> NAME/KEY: misc_feature
<223> OTHER INFORMATION: Strain name: SR1

<400> SEQUENCE: 2

Met Thr Thr Thr Pro Ile Ala Asn His Pro Asn Ile Phe Thr His Gln
1               5                   10                  15

Ser Ser Ser Ser Pro Leu Ala Phe Leu Asn Arg Thr Ser Phe Ile Pro
            20                  25                  30

Phe Ser Ile Ser Lys Arg Asn Ser Val Asn Cys Asn Gly Trp Arg
        35                  40                  45

Thr Arg Cys Ser Val Ala Lys Asp Tyr Thr Val Pro Ser Ser Ala Val
    50                  55                  60

Asp Gly Gly Pro Ala Ala Glu Leu Asp Cys Val Ile Val Gly Ala Gly
65                  70                  75                  80

Ile Ser Gly Leu Cys Ile Ala Gln Val Met Ser Ala Asn Tyr Pro Asn
```

```
                    85                  90                  95
Leu Met Val Thr Glu Ala Arg Asp Arg Ala Gly Gly Asn Ile Thr Thr
                100                 105                 110
Val Glu Arg Asp Gly Tyr Leu Trp Glu Glu Gly Pro Asn Ser Phe Gln
                115                 120                 125
Pro Ser Asp Pro Met Leu Thr Met Ala Val Asp Cys Gly Leu Lys Asp
            130                 135                 140
Asp Leu Val Leu Gly Asp Pro Asn Ala Pro Arg Phe Val Leu Trp Lys
145                 150                 155                 160
Gly Lys Leu Arg Pro Val Pro Ser Lys Leu Thr Asp Leu Pro Phe Phe
                165                 170                 175
Asp Leu Met Ser Ile Pro Gly Lys Leu Arg Ala Gly Phe Gly Pro Ile
            180                 185                 190
Gly Leu Arg Pro Ser Pro Gly His Glu Glu Ser Val Glu Gln Phe
                195                 200                 205
Val Arg Arg Asn Leu Gly Gly Glu Val Phe Glu Arg Leu Ile Glu Pro
            210                 215                 220
Phe Cys Ser Gly Val Tyr Val Gly Asp Pro Ser Lys Leu Ser Met Lys
225                 230                 235                 240
Ala Ala Phe Gly Lys Val Trp Lys Leu Glu Glu Thr Gly Gly Ser Ile
                245                 250                 255
Ile Gly Gly Thr Phe Lys Ala Ile Lys Glu Arg Ser Ser Thr Pro Lys
            260                 265                 270
Ala Pro Arg Asp Pro Arg Leu Pro Lys Pro Lys Gly Gln Thr Val Gly
            275                 280                 285
Ser Phe Arg Lys Gly Leu Arg Met Leu Pro Asp Ala Ile Ser Ala Arg
        290                 295                 300
Leu Gly Ser Lys Leu Lys Leu Ser Trp Lys Leu Ser Ser Ile Thr Lys
305                 310                 315                 320
Ser Glu Lys Gly Gly Tyr His Leu Thr Tyr Glu Thr Pro Glu Gly Val
                325                 330                 335
Val Ser Leu Gln Ser Arg Ser Ile Val Met Thr Val Pro Ser Tyr Val
            340                 345                 350
Ala Ser Asn Ile Leu Arg Pro Leu Ser Val Ala Ala Asp Ala Leu
        355                 360                 365
Ser Asn Phe Tyr Tyr Pro Pro Val Gly Ala Val Thr Ile Ser Tyr Pro
        370                 375                 380
Gln Glu Ala Ile Arg Asp Glu Arg Leu Val Asp Gly Glu Leu Lys Gly
385                 390                 395                 400
Phe Gly Gln Leu His Pro Arg Thr Gln Gly Val Glu Thr Leu Gly Thr
                405                 410                 415
Ile Tyr Ser Ser Ser Leu Phe Pro Asn Arg Ala Pro Lys Gly Arg Val
            420                 425                 430
Leu Leu Leu Asn Tyr Ile Gly Gly Ala Lys Asn Pro Glu Ile Leu Ser
        435                 440                 445
Lys Thr Glu Ser Gln Leu Val Glu Val Asp Arg Asp Leu Arg Lys
    450                 455                 460
Met Leu Ile Lys Pro Lys Ala Gln Asp Pro Leu Val Val Gly Val Arg
465                 470                 475                 480
Val Trp Pro Gln Ala Ile Pro Gln Phe Leu Val Gly His Leu Asp Thr
            485                 490                 495
Leu Ser Thr Ala Lys Ala Ala Met Asn Asp Asn Gly Leu Glu Gly Leu
            500                 505                 510
```

```
Phe Leu Gly Gly Asn Tyr Val Ser Gly Val Ala Leu Gly Arg Cys Val
         515                 520                 525

Glu Gly Ala Tyr Glu Val Ala Ser Glu Val Thr Gly Phe Leu Ser Arg
         530                 535                 540

Tyr Ala Tyr Lys
545

<210> SEQ ID NO 3
<211> LENGTH: 1874
<212> TYPE: DNA
<213> ORGANISM: Nicotiana tabacum
<220> FEATURE:
<221> NAME/KEY: exon
<222> LOCATION: (26)..(1672)
<221> NAME/KEY: misc_feature
<223> OTHER INFORMATION: Strain name: SR1

<400> SEQUENCE: 3
agcgcggtct acaagtcagg cagtc atg aca aca act ccc atc gcc aat cat      52
                            Met Thr Thr Thr Pro Ile Ala Asn His
                              1               5 cct aat att ttc act cac cag tcg tcg tca tcg cca ttg gca ttc tta     100
Pro Asn Ile Phe Thr His Gln Ser Ser Ser Ser Pro Leu Ala Phe Leu
 10              15                  20                  25 aac cgt acg agt ttc atc cct ttc tct tca atc tcc aag cgc aat agt     148
Asn Arg Thr Ser Phe Ile Pro Phe Ser Ser Ile Ser Lys Arg Asn Ser
                 30                  35                  40 gtc aat tgc aat ggc tgg aga aca cga tgc tcc gtt gcc aaa gat tac     196
Val Asn Cys Asn Gly Trp Arg Thr Arg Cys Ser Val Ala Lys Asp Tyr
             45                  50                  55 aca gtt cct tcc tca gcg gtc gac ggc gga ccc gcc gcg gag ctg gac     244
Thr Val Pro Ser Ser Ala Val Asp Gly Gly Pro Ala Ala Glu Leu Asp
         60                  65                  70 tgt gtt ata gtt gga gca gga att agt ggc ctc tgc att gcg cag gtg     292
Cys Val Ile Val Gly Ala Gly Ile Ser Gly Leu Cys Ile Ala Gln Val
     75                  80                  85 atg tcc gct aat tac ccc aat ttg atg gta acc gag gcg aga gat cgt     340
Met Ser Ala Asn Tyr Pro Asn Leu Met Val Thr Glu Ala Arg Asp Arg
 90                  95                 100                 105 gcc ggt ggc aac ata acg act gtg gaa aga gac ggc tat ttg tgg gaa     388
Ala Gly Gly Asn Ile Thr Thr Val Glu Arg Asp Gly Tyr Leu Trp Glu
                110                 115                 120 gaa ggt ccc aac agt ttc cag ccg tcc gat cct atg ttg act atg gca     436
Glu Gly Pro Asn Ser Phe Gln Pro Ser Asp Pro Met Leu Thr Met Ala
            125                 130                 135 gta gat tgt gga ttg aag gat gat ttg gtg ttg gga gat cct aat gcg     484
Val Asp Cys Gly Leu Lys Asp Asp Leu Val Leu Gly Asp Pro Asn Ala
        140                 145                 150 ccc cgt ttc gtt ttg tgg aag ggt aaa tta agg ccc gtc ccc tca aaa     532
Pro Arg Phe Val Leu Trp Lys Gly Lys Leu Arg Pro Val Pro Ser Lys
    155                 160                 165 ctc act gat ctt ccc ttt ttt gat ttg atg agc att cct ggc aag ttg     580
Leu Thr Asp Leu Pro Phe Phe Asp Leu Met Ser Ile Pro Gly Lys Leu
170                 175                 180                 185 aga gct ggt ttt ggt gcc att ggc ctc cgc cct tca cct cca ggt cat     628
Arg Ala Gly Phe Gly Ala Ile Gly Leu Arg Pro Ser Pro Pro Gly His
                190                 195                 200 gag gaa tca gtt gag cag ttc gtg cgt cgt aat ctt ggt ggc gaa gtc     676
Glu Glu Ser Val Glu Gln Phe Val Arg Arg Asn Leu Gly Gly Glu Val
            205                 210                 215
```

-continued

| | |
|---|---|
| ttt gaa cgc ttg ata gaa cca ttt tgt tct ggt gtt tat gtt ggt gat<br>Phe Glu Arg Leu Ile Glu Pro Phe Cys Ser Gly Val Tyr Val Gly Asp<br>220                       225                     230 | 724 |
| ccc tca aaa ctg agt atg aaa gca gca ttt ggg aaa gtt tgg aag ttg<br>Pro Ser Lys Leu Ser Met Lys Ala Ala Phe Gly Lys Val Trp Lys Leu<br>235                       240                   245 | 772 |
| gaa gaa act ggt ggt agc att att gga gga acc ttt aaa gca ata aag<br>Glu Glu Thr Gly Gly Ser Ile Ile Gly Gly Thr Phe Lys Ala Ile Lys<br>250                     255                   260               265 | 820 |
| gag aga tcc agt aca cct aaa gcg ccc cgc gat ccg cgt tta cct aaa<br>Glu Arg Ser Ser Thr Pro Lys Ala Pro Arg Asp Pro Arg Leu Pro Lys<br>                   270                   275                   280 | 868 |
| cca aaa gga cag aca gtt gga tca ttc agg aag ggt ctc aga atg ctg<br>Pro Lys Gly Gln Thr Val Gly Ser Phe Arg Lys Gly Leu Arg Met Leu<br>                   285                   290                   295 | 916 |
| ccg gat gca atc agt gca aga ttg gga agc aaa tta aaa cta tca tgg<br>Pro Asp Ala Ile Ser Ala Arg Leu Gly Ser Lys Leu Lys Leu Ser Trp<br>300                     305                   310 | 964 |
| aag ctt tct agc att act aag tca gaa aaa gga gga tat cac ttg aca<br>Lys Leu Ser Ser Ile Thr Lys Ser Glu Lys Gly Gly Tyr His Leu Thr<br>315                     320                   325 | 1012 |
| tac gag aca cca gaa gga gta gtt tct ctt caa agt cga agc att gtc<br>Tyr Glu Thr Pro Glu Gly Val Val Ser Leu Gln Ser Arg Ser Ile Val<br>330                     335                   340               345 | 1060 |
| atg act gtg cca tcc tat gta gca agc aac ata tta cgt cct ctt tcg<br>Met Thr Val Pro Ser Tyr Val Ala Ser Asn Ile Leu Arg Pro Leu Ser<br>                   350                   355                   360 | 1108 |
| gtt gcc gca gca gat gca ctt tca aat ttc tac tat ccc cca gtt gga<br>Val Ala Ala Ala Asp Ala Leu Ser Asn Phe Tyr Tyr Pro Pro Val Gly<br>                   365                   370                   375 | 1156 |
| gca gtc aca att tca tat cct caa gaa gct att cgt gat gag cgt ctg<br>Ala Val Thr Ile Ser Tyr Pro Gln Glu Ala Ile Arg Asp Glu Arg Leu<br>380                     385                   390 | 1204 |
| gtt gat ggt gaa cta aag gga ttt ggg cag ttg cat cca cgt aca cag<br>Val Asp Gly Glu Leu Lys Gly Phe Gly Gln Leu His Pro Arg Thr Gln<br>395                     400                   405 | 1252 |
| gga gtg gaa aca cta gga acg ata tat agt tca tca ctc ttc cct aac<br>Gly Val Glu Thr Leu Gly Thr Ile Tyr Ser Ser Ser Leu Phe Pro Asn<br>410                     415                   420               425 | 1300 |
| cgt gcc cca aaa ggt cgg gtg cta ctc ttg aac tac att gga gga gca<br>Arg Ala Pro Lys Gly Arg Val Leu Leu Leu Asn Tyr Ile Gly Gly Ala<br>                   430                   435                   440 | 1348 |
| aaa aat cct gaa att ttg tct aag acg gag agc caa ctt gtg gaa gta<br>Lys Asn Pro Glu Ile Leu Ser Lys Thr Glu Ser Gln Leu Val Glu Val<br>                   445                   450                   455 | 1396 |
| gtt gat cgt gac ctc aga aaa atg ctt ata aaa ccc aaa gct caa gat<br>Val Asp Arg Asp Leu Arg Lys Met Leu Ile Lys Pro Lys Ala Gln Asp<br>460                     465                   470 | 1444 |
| cct ctt gtt gtg ggt gtg cga gta tgg cca caa gct atc cca cag ttt<br>Pro Leu Val Val Gly Val Arg Val Trp Pro Gln Ala Ile Pro Gln Phe<br>475                     480                   485 | 1492 |
| ttg gtt ggt cat ctg gat acg cta agt act gca aaa gct gct atg aat<br>Leu Val Gly His Leu Asp Thr Leu Ser Thr Ala Lys Ala Ala Met Asn<br>490                     495                   500               505 | 1540 |
| gat aat ggg ctt gaa ggg ctg ttt ctt ggg ggt aat tat gtg tca ggt<br>Asp Asn Gly Leu Glu Gly Leu Phe Leu Gly Gly Asn Tyr Val Ser Gly<br>                   510                   515                   520 | 1588 |
| gta gca ttg ggg agg tgt gtt gaa ggt gct tat gaa gtt gca tcc gag<br>Val Ala Leu Gly Arg Cys Val Glu Gly Ala Tyr Glu Val Ala Ser Glu<br>525                     530                   535 | 1636 |

-continued

```
gta aca gga ttt ctg tct cgg tat gca tac aaa tga aacctgtgtt      1682
Val Thr Gly Phe Leu Ser Arg Tyr Ala Tyr Lys
        540                 545 ggggtagtc caaaccttgt tagtagtacg atcatgcctt gggaaaattg gcatgtgcct  1742
aaaagttttg ctcattagag ttattttagc cttggtaaat gatttgtact tgatatcagt  1802
cgttttcttt gagataaaat gttcctgttc aggaaatata atgtatatca attttaaaca  1862
aaaaaaaaaa aa                                                     1874

<210> SEQ ID NO 4
<211> LENGTH: 23
<212> TYPE: DNA
<213> ORGANISM: Artificial Sequence
<220> FEATURE:
<223> OTHER INFORMATION: lambda-gt22A forward primer

<400> SEQUENCE: 4
attggtggcg acgactcctg gag                                         23

<210> SEQ ID NO 5
<211> LENGTH: 24
<212> TYPE: DNA
<213> ORGANISM: Artificial Sequence
<220> FEATURE:
<223> OTHER INFORMATION: lambda-gt22A reverse primer

<400> SEQUENCE: 5
ccagaccaac tggtaatggt agcg                                        24

<210> SEQ ID NO 6
<211> LENGTH: 24
<212> TYPE: DNA
<213> ORGANISM: Artificial Sequence
<220> FEATURE:
<223> OTHER INFORMATION: forward primer

<400> SEQUENCE: 6
gcggtctaca agtcaggcag tcat                                        24

<210> SEQ ID NO 7
<211> LENGTH: 31
<212> TYPE: DNA
<213> ORGANISM: Artificial Sequence
<220> FEATURE:
<223> OTHER INFORMATION: reverse primer

<400> SEQUENCE: 7
catgccaatt ttcccaaggc atgatcgtac t                                31

<210> SEQ ID NO 8
<211> LENGTH: 20
<212> TYPE: DNA
<213> ORGANISM: Artificial Sequence
<220> FEATURE:
<223> OTHER INFORMATION: mutagenic primer

<400> SEQUENCE: 8
ggtgtttatg ttggtgatcc                                             20

<210> SEQ ID NO 9
<211> LENGTH: 27
<212> TYPE: DNA
<213> ORGANISM: Artificial Sequence
<220> FEATURE:
```

<223> OTHER INFORMATION: CaMV 35S promoter forward primer

<400> SEQUENCE: 9
cacagatggt tagagaggct tacgcac                27

<210> SEQ ID NO 10
<211> LENGTH: 27
<212> TYPE: DNA
<213> ORGANISM: Artificial Sequence
<220> FEATURE:
<223> OTHER INFORMATION: Nos terminator reverse primer

<400> SEQUENCE: 10
tcatcgcaag accggcaaca ggattca                27

<210> SEQ ID NO 11
<211> LENGTH: 537
<212> TYPE: PRT
<213> ORGANISM: Arabidopsis thaliana

<400> SEQUENCE: 11

```
Met Glu Leu Ser Leu Leu Arg Pro Thr Thr Gln Ser Leu Leu Pro Ser
1               5                   10                  15

Phe Ser Lys Pro Asn Leu Arg Leu Asn Val Tyr Lys Pro Leu Arg Leu
            20                  25                  30

Arg Cys Ser Val Ala Gly Gly Pro Thr Val Gly Ser Ser Lys Ile Glu
        35                  40                  45

Gly Gly Gly Gly Thr Thr Ile Thr Thr Asp Cys Val Ile Val Gly Gly
    50                  55                  60

Gly Ile Ser Gly Leu Cys Ile Ala Gln Ala Leu Ala Thr Lys His Pro
65                  70                  75                  80

Asp Ala Ala Pro Asn Leu Ile Val Thr Glu Ala Lys Asp Arg Val Gly
                85                  90                  95

Gly Asn Ile Ile Thr Arg Glu Glu Asn Gly Phe Leu Trp Glu Glu Gly
            100                 105                 110

Pro Asn Ser Phe Gln Pro Ser Asp Pro Met Leu Thr Met Val Val Asp
        115                 120                 125

Ser Gly Leu Lys Asp Asp Leu Val Leu Gly Asp Pro Thr Ala Pro Arg
    130                 135                 140

Phe Val Leu Trp Asn Gly Lys Leu Arg Pro Val Pro Ser Lys Leu Thr
145                 150                 155                 160

Asp Leu Pro Phe Phe Asp Leu Met Ser Ile Gly Gly Lys Ile Arg Ala
                165                 170                 175

Gly Phe Gly Ala Leu Gly Ile Arg Pro Ser Pro Pro Gly Arg Glu Glu
            180                 185                 190

Ser Val Glu Glu Phe Val Arg Arg Asn Leu Gly Asp Glu Val Phe Glu
        195                 200                 205

Arg Leu Ile Glu Pro Phe Cys Ser Gly Val Tyr Ala Gly Asp Pro Ser
    210                 215                 220

Lys Leu Ser Met Lys Ala Ala Phe Gly Lys Val Trp Lys Leu Glu Gln
225                 230                 235                 240

Asn Gly Gly Ser Ile Ile Gly Gly Thr Phe Lys Ala Ile Gln Glu Arg
                245                 250                 255

Lys Asn Ala Pro Lys Ala Glu Arg Asp Pro Arg Leu Pro Lys Pro Gln
            260                 265                 270

Gly Gln Thr Val Gly Ser Phe Arg Lys Gly Leu Arg Met Leu Pro Glu
        275                 280                 285
```

-continued

```
Ala Ile Ser Ala Arg Leu Gly Ser Lys Val Lys Leu Ser Trp Lys Leu
    290                 295                 300

Ser Gly Ile Thr Lys Leu Glu Ser Gly Gly Tyr Asn Leu Thr Tyr Glu
305                 310                 315                 320

Thr Pro Asp Gly Leu Val Ser Val Gln Ser Lys Ser Val Val Met Thr
                325                 330                 335

Val Pro Ser His Val Ala Ser Gly Leu Leu Arg Pro Leu Ser Glu Ser
                340                 345                 350

Ala Ala Asn Ala Leu Ser Lys Leu Tyr Tyr Pro Pro Val Ala Ala Val
                355                 360                 365

Ser Ile Ser Tyr Pro Lys Glu Ala Ile Arg Thr Glu Cys Leu Ile Asp
    370                 375                 380

Gly Glu Leu Lys Gly Phe Gly Gln Leu His Pro Arg Thr Gln Gly Val
385                 390                 395                 400

Glu Thr Leu Gly Thr Ile Tyr Ser Ser Ser Leu Phe Pro Asn Arg Ala
                405                 410                 415

Pro Pro Gly Arg Ile Leu Leu Asn Tyr Ile Gly Gly Ser Thr Asn
                420                 425                 430

Thr Gly Ile Leu Ser Lys Ser Glu Gly Glu Leu Val Glu Ala Val Asp
                435                 440                 445

Arg Asp Leu Arg Lys Met Leu Ile Lys Pro Asn Ser Thr Asp Pro Leu
    450                 455                 460

Lys Leu Gly Val Arg Val Trp Pro Gln Ala Ile Pro Gln Phe Leu Val
465                 470                 475                 480

Gly His Phe Asp Ile Leu Asp Thr Ala Lys Ser Ser Leu Thr Ser Ser
                485                 490                 495

Gly Tyr Glu Gly Leu Phe Leu Gly Gly Asn Tyr Val Ala Gly Val Ala
                500                 505                 510

Leu Gly Arg Cys Val Glu Gly Ala Tyr Glu Thr Ala Ile Glu Val Asn
                515                 520                 525

Asn Phe Met Ser Arg Tyr Ala Tyr Lys
    530                 535
```

HERBICIDE-RESISTANT PROTOPORPHYRINOGEN OXIDASE ISOLATED FROM *NICOTIANA TABACUM*

FIELD OF THE INVENTION

The present invention relates to a novel protoporphyrinogen oxidase tolerant to light-requiring herbicide, a gene which codes the protein, a recombinant vector comprising the gene and a transformant by the vector.

BACKGROUND OF THE INVENTION

Protoporphyrinogen oxidase is an enzyme which convert protoporphyrinogen IX into protoporphyrin IX, in a tetrapyrrole synthesis system which exists universally in all organism.

In this synthesis system, heme is synthesized in case of a microorganism and an animal, on the other hand, chlorophyll in addition to heme is synthesized in case of a plant. This enzyme is thought to be a target enzyme of photobleaching herbicide, and the identification of the enzyme and the isolation of the gene has not been performed until now. HemG of *E. coli* has been isolated as a protoporphyrinogen oxidase gene in 1993 (Sasarman, A. et al (1993) *Can. J. Microbiol.* 39:1156–1161.), and HemY of *B.subtilis* has been isolated as a protoporphyrinogen oxidase gene in 1994 (Dailey, T. A. et al. (1994) *J. Biol. Chem.* 269:813–815.). In eukaryote, cloning of human protoporphyrinogen oxidase gene has been conducted in 1995 (Nishimura, K. et al. (1995) *J. Biol. Chem.* 270:8076–8080.), and in the same year, cloning of mouse protoporphyrinogen oxidase gene has been conducted (Taketani, S. et al. (1995) *Eur. J. Biochem.* 230:760–765.). In plant, cloning of *Arabidopsis thaliana* and corn protoporphyrinogen oxidase gene has been conducted in 1995 (WO 96/34659).

Further, a gene of *Arabidopsis thaliana* . . . Heynh. and corn protoporphyrinogen oxidase tolerant to photobleaching herbicide has already been obtained by screening system using *E. coli*.

The screening of a gene of *Arabidopsis thaliana* and corn protoporphyrinogen oxidase tolerant to photobleaching herbicide (WO 95/34659) has been done by using *E. coli*. Thus, it is not clear whether sufficient activity of such gene can be performed in a plant cell, and whether the tolerance is sufficient.

DISCLOSURE OF THE INVENTION

When a plant tolerant to photobleaching herbicide is produced by using a recombinant DNA technique, the protoporphyrinogen oxidase gene tolerant to photobleaching herbicide, derived from a higher plant can be a strong candidate. Protoporphyrinogen oxidase derived from the other organism is largely different, for example, the protoporphyrinogen oxidase derived from *E. coli* is different in that the molecular weight is apparently smaller compared with the enzyme from other organism. The protoporphyrinogen oxidase derived from *B. subtilis* is soluble and very different from a membrane-bound type protoporphyrinogen oxidase from the other organism in that the former is soluble.

Further, the protoporphyrinogen oxidase derived from an animal has special nature that it is transported into mitochondria, in spite that it has no transit peptide.

In producing a plant tolerant to photobleaching herbicide by using recombinant DNA technique, using of the protoporphyrinogen oxidase which is derived from a higher plant is preferable, in view of such differences of the nature in the protoporphyrinogen oxidase derived from each organism.

On the other hand, it is not clear whether the resistant gene (WO 97/04088) derived from *Chlamydomonas*, an unicellular organism, is protoporphyrinogen oxidase, and whether the gene can give a tolerance to a higher plant.

Therefore, preferable gene is thought to be such a gene obtained from a process in which a plant cell or a plant is screened with herbicides, the resistant type gene in the plant cell or plant body is confirmed to have a sufficient biological activity and a high tolerance to photobleaching herbicide in a plant cell, then, the gene is isolated by using a certain method.

Accordingly, the problem of the present invention is to provide a protoporphyrinogen oxidase highly tolerant to photobleaching herbicides, a gene encoding the enzyme, a recombinant vector comprising the gene and a transformant by the vector.

The present inventors have extensively studied about a higher plant protoporphyrinogen oxidase to solve the above-described problem. As the result, the present inventors have taken a steps in which a plant cell of plant body is screened under the existence of herbicides, the resistant type gene in the plant cell or plant body is confirmed to have a sufficient biological activity and a high tolerancey to photobleaching herbicide in a plant cell, then, the gene is isolated by using a certain method. In more detail, the present inventors have extensively studied about protoporphyrinogen from a higher plant, especially tobacco to solve the above-described problem. As the result, the present inventors have succeeded in cloning of protoporphyrinogen oxidase tolerant to photobleaching herbicide from tobacco. The gene of the present invention is novel, and when tolerance of the gene product to photobleaching herbicide is compared with the tolerance of the known protoporphyrinogen oxidase derived from *Arabidopsis thaliana*, it has now been found that the tolerance of the present gene product is very superior, in spite of large structural similarity of both genes. Accordingly, the above-described problems can be solved by using the gene of the present invention.

The present invention provides protoporphyrinogen oxidase, derivatives thereof or mutants thereof, comprising the amino acid sequence represented by SEQ-ID No.2 or mutated peptide derived therefrom by deletion, addition, substitution, etc. of one or more amino acids in the above amino acid sequence and having an enzyme activity substantially equivalent to that of the protoporphyrinogen oxidase tolerant to photobleaching herbicide.

The protoporphyrinogen oxidase of the present invention comprising the amino acid sequence represented by SEQ ID No.2 includes mutated peptide in which deletion, addition, substitution, etc. of one or more amino acids in the above amino acid sequence is observed, that is, mutated peptide discovered in the nature or artificially modified mutated peptide, provided that the mutated peptide is not damaged in substantially same enzyme activity and tolerance to photobleaching herbicide.

The present polypeptide is thought to be an enzyme existing in a chloroplast. In general, almost all protein existing in intracellular organelle, such as a chloroplast, is encoded in a genome of nuclear, and it is translated in cytoplasm, then, by the function of a transportation signal, called transit peptide, existing in N-terminal, it is transported to these intracellular organelle. After the transportation, the transit peptide is cleaved to become a mature protein. Accordingly, it can be thought that transit peptide exists in N-terminal of the polypeptide of the present invention. Further, essential part by which biological activity is expressed is a part in which transit peptide is excluded, i.e., a mature protein, thus, the transit peptide does not relate to the activity. Accordingly, the present invention comprises a mature protein in which transit peptide is deleted.

In more detail, the present invention provides the protoporphyrinogen oxidase gene comprising the nucleotide sequence represented by SEQ ID No.3 or the nucleotide sequence in which one or more nucleotide in the above nucleotide sequence is deleted, added, or substituted and which encode a polypeptide having an activity substantially equivalent to that of the protoporphyrinogen oxidase.

Further, the DNA sequence encoding the above polypeptide of the present invention includes cDNA encoding objective protoporphyrinogen oxidase, chromosomal DNA comprising intron and exon, DNA in which exon is connected with exclusion of intron, and further a synthetic DNA which is obtained by connecting oligonucleotide prepared artificially using a synthetic DNA method. When a synthetic DNA is prepared by using the synthetic DNA method, the objective DNA can be prepared by degeneration of genetic code, and by changing the nucleotide sequence of the gene, without changing encoding amino acid. Thus, the DNA of the present invention comprises all nucleotide sequences which is based on the degeneration of the gene encoding the objective polypeptide.

Further, present invention provides a recombinant vector comprising the above-described gene, a transformant by the above-described vector.

BEST MODE FOR UTILIZATION OF THE INVENTION

Figure 1:
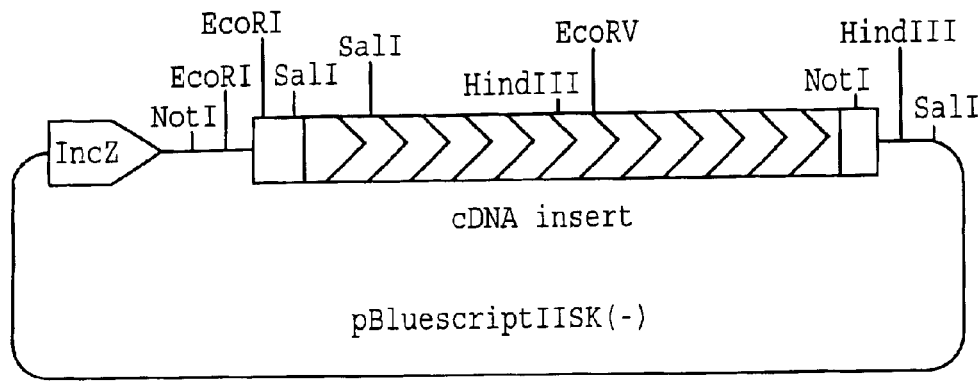
FIG. 1 is schematic figure of pBNtPX-1

Hereinafter, the invention is described in more detail.

The general procedures for plant cell and tissue culture, or series of biological procedures, such as purification of mRNA, preparation of cDNA, cDNA library, recombinant DNA, determination of nucleotide sequence of DNA, or plant biological procedures, such as transformation of plant can be performed according to known literatures, for example, *Plant Cell and Tissue Culture*, Vasil, I. K. and Thorpe, T. A. Kluwer Academic Publishers, 1994 etc., or *Molecular Cloning* 2$^{nd}$ Edition, CSH Laboratory Press, Sambrook, J. et al., 1989, *Current Protocols in Molecular Biology*, John Wiley & Sons, Ausubel, M. et al. etc., or *Plant Molecular Biology Manual*, Gelvin, S. A. et al. Kluwer Academic Publishers, 1991, 1995 (Second edition) etc.

1. Photobleaching Herbicide

The photobleaching herbicide used in the present invention is a herbicide which requires light for expressing herbicidal activity. When the photobleaching herbicide is applied to a plant, at first, the membrane in a cell is destroyed peroxidatively, then terrestrial part becomes white, and withered at last. In a cell treated by photobleaching herbicide, protoporphyrin IX was found to be accumulated (Matringe, M. And Scalla, R. (1988) *Plant Physiol.* 86:619–622.), and it became clear by the study thereafter that the target enzyme of the photobleaching herbicide is protoporphyrinogen oxidase which convert protoporphyrinogen IX to protoporphin IX in tetrapyrrole synthesis system (Matringe, M. et al. (1989) *Biochem, J.* 260:231–235.). At present, mode of action of the photobleaching herbicide is thought to be as follows. When the protoporphyrinogen oxidase in a plant cell is inhibited by a photobleaching herbicide, at first protoporphyrinogen IX, a substrate, is accumulated, then, protoporphyrin IX is produced in large amount from this protoporphyrinogen IX, non-enzymatically or by non-specific oxidation enzyme in the cytoplasm, which is non-sensitive to the photobleaching herbicide. This protoporphyrin IX introduces a photosensitization reaction under light, a large amount of active oxygen is generated, and it destroys a membrane peroxidatively to cause a plant wither (Scalla, R. and Matringe, Mm. (1994) *Rev. Weed Sci.* 6:103–132). From these mode of action, photobleaching herbicide is also called as a protoporphyrinogen oxidase (Protox) inhibitor or a porphyrin-generating type herbicide.

Compound having wide variety of structures belong to the photobleaching herbicides. As the representative compound, diphenyl ether series, oxadiazole series, pyridine series, pyrimidine series, cyclic imide series, triazole series, pyrazole series (Scalla, R. and Matringe, M. (1994) *Rev. Weed Sci.* 6:103–132) are included.

As the photobleaching herbicide of the present invention, triazole series and pyrazole series are preferable, and the pyrazole series compounds described below are most preferable.

Compound Name

English name: ethyl 2-chloro-5-(4-chloro-5-difluoromethoxy-1-m ethyl-1H-pyrazol-3-yl)-4-fluorophenoxyacetate (hereinafter referred to as Compound A. Described in Toku Kai Hei 3-163063)

English name: ethyl 2-[5-(4-chloro-5-difluoromethoxy-1-methyl-1H-pyrazol-3-yl)-2,4-dichloro-phenylamino] propionate (hereinafter referred to as Compound B. Described in Toku Kai Hei 3-163063)

English name: 4-chloro-3-(4-chloro-2-fluoro-5-methoxyphenyl)-5-difluoromethoxy-1-methyl-1H-pyrazole (hereinafter referred to as Compound C. Described in Toku Kai Hei 4-225937)

English name: 4-chloro-3-[4-chloro-2-fluoro-5-(2-propynyl)oxyp henyl]-5-difluoromethoxy-1-methyl-1H-pyrazole (hereinafter referred to as Compound D. Described in Toku Kai Hei 3-163063)

English name: ethyl 2-[2-chloro-5-(4-chloro-5-difluoromethoxy-1-methyl-1H-pyrazol-3-yl)-4-fluorophenoxy]propionate (hereinafter referred to as Compound E. Described in Toku Kai Hei 3-163063)

English name: 1-methylethyl 5-[4-bromo-1-methyl-5-(trifluorome thyl)-1H-pyrazol-3-yl]-2-chloro-4-fluorobenzoate (hereinafter referred to as Compound F. Described in Toku Hyo Hei 10-502926)

English name: 4-chloro-3-(4-chloro-2-fluorophenyl)-5-difluorom ethoxy-1-methyl-1H-pyrazole (hereinafter referred to as Compound G. Described in Toku Kai Hei 3-72460)

2. Screening of Tobacco Callus Tolerant to Photobleaching Herbicide

A plant can be differentiated from a protoplast, a cell, to a complete plant body, through callus which is a mass of cells. Such nature that a plant has is called as totipotency.

Further, as a characteristic of a plant cell in culture, it can be pointed out that the cell is very mutative, and such mutation is called as somaclonal variation. Accordingly, if such culturing cell is screened by a certain compound, for example, a herbicide, a herbicide-tolerant cell can be obtained. Further, the obtained herbicide-tolerant cell can be regenerated to a plant body by utilizing the totipotency. Many examples, such as, a glyphosate tolerant plant (Singer, S. R. And Mcdaniel, C. N. (1985) *Plant Physiol.* 78:411–416), a sulfonylurea tolerant plant (Chaleff, R. S. And Ray, T. B. (1984) *Science* 223:1148–1151), etc. are known. However, there are many cases that a culturing cell loses the totipotency by some reason during the culture. Further, it is difficult to introduce the herbicide tolerance into a plant of different species by using such methods. Thus, if a gene reponsible to the tolerance to herbicide can be isolated from a cell tolerant to herbicide, the obtained gene can be introduced into several useful crops by known method, such as, the *Agrobacterium* method. As such a herbicide-tolerant gene, the following genes are known: a gene encoding an enzyme which detoxify the herbicide itself, for example, bromoxynil detoxifying enzyme gene (Stalker, D. M. et al. (1988) *Science* 242:419–423.), bialaphos detoxifying enzyme gene (De Block, M. et al. (1987) EMBO J. 6:2513–2518); and a gene encoding an enzyme which detoxify some toxic substance produced by a herbicide, for example, superoxide dismutase gene (Furusawa, I. et al. (1987) *Plant Cell Physiol.* 25:1247–1252.); a herbicide tolerant type target enzyme gene, for example, sulfonylurea tolerant type acetolactate synthase (ALS) gene (Lee, K. Y. et al. (1988) EMBO, J. 7:1241–1248.), glyphosate tolerant type 5-enolpyruvylshikimate-3-phosphate synthase (EPSPS) gene (Comai, L. et al. (1985) *Nature* 317:741–744) etc.

3. Mode of Action of Herbicide Tolerance in Culturing Cell

As a mode of action of tolerance in culturing cell tolerant to a herbicide, acquisition of detoxification mechanism, change of drug permeability into a cell, over production of target enzyme and mutation of the target enzyme into herbicide tolerant type, etc. can be thought. On what mechanism the tolerance is based can be assumed by reviewing the presence of the accumulation of a precursor in the reaction which herbicides inhibit; by comparing tolerance against herbicides having various structures which show the same of different mode of action; by extracting a target enzyme from both tolerant cell and sensitive cell and comparing the enzyme activity; and by reviewing the sensitivity of the target enzyme in vitro against the herbicide used in the screening. As a result, if it have become clear that an useful herbicide tolerant gene exists, it becomes a useful gene source for isolating a herbicide tolerant gene.

4. Cloning Method of the Gene

As a method for cloning a gene, there is a method in which protein information is utilized, a method in which nucleic acid information is utilized and a genetical method. As the method in which protein information is utilized, there is a method in which a target protein is purified, and the expression library is screened out by using an antibody thereof, a method in which the amino acid sequence of the target protein is identified even in partial, and from the information, an oligonucleotide probe or a PCR primer is synthesized. However, it is generally difficult to purify a protein. On the other hand, a method in which nucleic acid information is utilized is one in which the objective gene is isolated, by utilizing gene homology among organisms, by using a gene of the other organism as a probe, and by using the hybridization method. The gene homology among organisms varies depending on the organism used and the gene used, and the condition of the hybridization is experimentally determined after carrying out under various conditions. It can be a case that the best condition can not be determined. Further, in these methods, it is necessary to confirm the biological activity of the obtained gene product by using some other methods.

On the other hand, the genetical method is a method in which the gene encoding a protein with tha same function derived from a different organism is introduced into a mutated microorganism in which the objective gene is genetically deleted, such as *E. coli, B. subtilis* and yeast etc., in such a manner that it can be expressed in the organism, and the growth is complemented. This method is also called as the genetically complementary method, the biological activity of the gene product is already confirmed, at time of isolating the gene. However, when a gene derived from a higher organism is expressed in a microorganism, there is a case that the growth is not complemented, by the reason that the modification, for example the addition of a sugar chain, is not achieved and can not perform the enzyme activity, or the enzyme activity can not be achieved because that the protein derived from the vector or transit peptide: is added to the N-terminal. Nevertheless, in the tetrapyrrole system in a plant, Glu-tRNA Reductase which synthesizes Glutamate-1-semialdehyde from Glu-tRNA, and Glutamate-1-semialdehyde aminotansferase which synthesizes 5-Aminolevulinic acid from Glutamate-1-semialdehyde, are cloned by the genetically complementation method, respectively by using *E. coli* hemA gene deleted mutant strain and hemL gene deleted mutant strain. (IIag, L. L. et al., (1994) *Plant Cell* 6:265–275). Thus, it can be thought to be effective to use a gene deleted mutant strain of *E. coli.* in isolating plant protoporphyrinogen oxidase. As an *E. coli* mutant strain in which protoporphyrinogen oxidase is deleted, SASX38 (Sasarman, A. et al. (1979) *J. Gen. Microbiol.* 113:297–303) and VSR751 (Nishimura, K. et al. (1995) *J. Bio. Chem.* 270:6076–8080), a mutant strain in which hemg gene is deleted, is known.

5. Preparation Method for cDNA Library

Total RNA of a plant can be extracted from a plant body, by using known methods, for example, guanidine method, guanidine phenol method, SDS phenol method, etc. Further, mRNA can be purified by conventional methods, for example, oligo dT cellulose method, etc.

The preparation of cDNA can be performed according to the conventional method as described in the above literatures. The double stranded cDNA can be synthesized using the purified mRNA as a template by Okayama-Berg method, Gubler-Hoffman method etc.

The cDNA library can be prepared according to the conventional method, by ligating the cDNA with a plasmid or λ phage etc. It is preferable that a vector which has a promoter, such as, λ phage lacZ, tac, at upstream of MCS, is selected (for example, pUC series plasmid and λgt11 series phage etc.), and to prepare an expression type cDNA library. Further, unidirectional library can be prepared by using a primer-adaptor etc. as a primer.

6. Cloning and Analysis of cDNA of Protoporphyrinogen Oxidase

The protoporphyrinogen oxidase gene can be cloned, by introducing the expression type cDNA library into an *E. coli* mutant strain in which hemG (protoporphyrinogen oxidase gene) is deleted, and isolating a cDNA clone which complements the growth. The whole DNA sequence of the gene thus cloned can be determined by Maxiam-Gilbert method or Sanger method. Further, the search for protein coding region, and the analysis of homology of the nucleotide sequence with known genes can be performed by using a commercially available software for analysis of a nucleotide sequence, for example, GENETYX (SDC Co. Ltd.,) or DNASIS (Hitachi software engineering Co., Ltd.).

7. Cloning of the Gene of Protoporphyrinogen Oxidase Tolerant to Photobleaching Herbicide from a Callus Tolerant to Photobleaching Herbicide In case that the protoporphyrinogen oxidase gene is cloned from a tobacco callus having a tolerance mechanism to photobleaching herbicide, caused from the conversion of protoporphyrinogen oxidase into a tolerant type to a photobleaching herbicide, the construction of cDNA library and the genetically complementary method is not necessarily needed, the cloning is relatively easily performed by PCR. The cloning of the protoporphyrinogen oxidase gene having a biological activity and the subcloning into a plasmid vector can relatively easily be conducted by designing a PCR primer which can amplify the whole open reading frame encoding protoporphyrinogen oxidase, from the nucleotide sequence information of the tobacco chloroplast type protoporphyrinogen oxidase gene disclosed by the present invention; then by conducting RT-PCR (mRNA is converted to cDNA by a reverse transcriptase, and PCR thereof is performed.) by using these primers.

The extent of tolerance of thus obtained gene is relatively easily examined by introducing the obtained plasmid into the mutant strain of E. colihaving a deletion of hemG, and by comparing the extent of inhibition of growth of the obtained E. coli by the photobleaching herbicide.

8. Production of a Plant Tolerant to Photobleaching Herbicides

By using the protoporphyrinogen oxidase gene which is tolerant to a photobleaching herbicide disclosed by the present invention, a plant which is tolerant to photobleaching herbicides can be produced. That is, a transformed plant can be produced by incorporating into a appropriate plasmid vector an expression cassette comprising a promoter capable of working in a plant cell, the protoporphyrinogen oxidase gene which is tolerant to photobleaching herbicides, and a terminator capable of working in a plant cell; by incorporating the expression cassette using known gene incorporation methods, such as, the *Agrobacterium* method, the electroporation method into a protoplast and the particle gun method, etc. Thus obtained plant has an agriculturally useful character of the tolerance to photobleaching herbicides. Further, when a expression cassette which has a different gene is used simultaneously, the nature to be tolerant to photobleaching herbicides can be utilized as a selected marker of the transformed plant.

As the appropriate plasmid vector, pBI plasmid or pMON plasmid can be listed in case of using the *Agrobacterium* method, and pUC plasmid and pBluescript plasmid can be listed in case of using the other method. Further, as the promoter capable of work in a plant, a cauliflower mosaic virus (CaMV) 35S promoter can be listed, and as the terminator capable of working in a plant, a CaMV terminator can be listed. Detailed explanation is described in the above-described experimental text books, such as *Plant Molecular Biology manual*, Gelvin, S. A. et al., Kluwer Academic Publishers, 1991, 1995 (Second edition) etc.

EXAMPLES

Hereinafter the present invention is described in more detail by showing examples, but the present invention is not limited to these examples.

Example 1

Selection of Tobacco Callus Tolerant to Photobleaching Herbicide

A. Preparation of Tobacco Callus and Regeneration of the Callus and Study of Sensitivity to Photobleaching Herbicide Tobacco (*Nicotiana tabacum* CV. Xanthi NC) was grown to 40 cm tall in a green house. And a leaf was cut, and the leaf was cut to square-shape of 5 cm width by a knife, then immersed in 70% ethanol for 30 seconds and in an aqueous solution of sodium hypochlorite (the effective concentration of chlorine was 1%) for 15 minutes to conduct surface-sterilization. After washing it for three times by sterilized water and removal of epidermis, the leaf fragment was suspended in 0.6M manitol (pH 5.8) containing an enzyme solution (1% cellulase onozuka R-10 and 0.05% macerozyme R-10 (manufactured by Yakult Co., Ltd.)) at 26° C. for three hours. After the enzyme treatment, protoplasts were washed with centrifugation by Murasige-Skoog (MS) medium for three times, and the obtained protoplast was suspended into MS solid medium containing 0.6% agar and 1 ppm of NAA and BA, to make a cell number of $10^8$/ml, and pored into a dish at 1 cm thick. The protoplast was cultured at 27° C. under darkness to regenerate a callus. Four weeks after the incubation, the agar medium containing a callus grown up to about 1 mm large, was cut to rectangular shape having 1 cm width, and put on MS solid medium containing various concentration of the compound H (4-chloro-3-[2,4-dichloro-5(2-propenyloxy)phenyl]-5-difluoromethoxy-1-methyl-1H-pyrazole, described in Toku Kai Hei 3-163063), and the sensitivity of tobacco callus to photobleaching herbicide was examined. As shoen in Table 1, it become apparent that the callus completely dies at 10 nM.

TABLE 1

Sensitivity of tobacco callus to the compound H

| Conc. (nM) | Survival Rate (%) |
|---|---|
| 0 | 100 |
| 2.5 | 30 |
| 5 | 10 |
| 10 | 0 |
| 20 | 0 |
| 40 | 0 |
| 8 | 0 |

B. Selection of Callus Highly Resistant to Photobleaching Herbicide

Using a medium containing the compound H containing two times concentration (20 nM) of the concentration at which tobacco callus completely dies, the selection of tobacco callus tolerant to photobleaching herbicide has been started. $1 \times 10^5$ of tobacco callus have been selected (Table 2), in the course of re-generation from $1 \times 10^{10}$ of the protoplast. Thus obtained resistant callus was transplanted into media having an increasing concentration of compound H, and thirty six cell lines which can be grown at even 2,400 nM were obtained finally, and three cell lines (EtR-056, RTR-245 and ETR-253), growth of which were especially superior were selected.

TABLE 2

Selection course of a strain tolerant to the photobleaching herbicide

| Conc. (nM) | Number of resistant cell lines |
|---|---|
| 20 | 100,000 |
| 30 | 50,000 |
| 50 | 40,000 |
| 75 | 7,200 |
| 150 | 254 |
| 300 | 120 |
| 600 | 66 |
| 1200 | 46 |
| 2,400 | 36 |
| 5,000 | 0 | number of protoplast given: $1 \times 10^{10}$

Example 2

Analysis of the Resistant Mechanism of the Callus Tolerant to Photobleaching Herbicide A. Accumulation of Protoporphyline IX in Photobleaching Herbicide Resistant Cell Lines The present inventors have tried to analyze the resistant mechanism in the resistant strain tolerant to photobleaching herbicide. It has been reported that in a plant treated by photobleaching herbicide, protoporphyrin IX is accumulated, the present inventors tried to measure the accumulation of protoporphyrin IX periodically. A resistant callus which has been subcultured in MS liquid medium containing 1,200 nM of compound H under light condition was cultured for 24 hours in a dark condition, then transplanted into MS liquid medium containing 1,200 nM of compound H, and after 6, 12, 18, 24, 32 and 48 hours later, the callus was collected, and protoporphyrin IX was measured. The extraction and assay of the protoporphyrin 1x from the callus were conducted as follows (Matringe, M. et al. (1989) *Biochem, J.* 260:231–235.). That is, 500 mg (wet weight) of the callus was homogenized in a mortar, and extracted with 7.5 ml of acetone: 1N $NH_4OH$ (9:1). The extract was centrifuged at 3,000×g for 10 minutes, then the supernatant was collected. To the supernatant 2.5 ml of hexane was added and mixed sufficiently, then, the lower layer was recovered. Further, after washing with hexane two twice, the amount of protoporphyrin IX obtained in the lower layer was measured from the value of Ex 405 nm-Em 631.5 nm by a fluorescence spectrophotometer. All the extraction procedures were conducted under the safety light.

As a result, the amount of protoporphyrin IX was 1.3 µg/g fresh weight at 24 hours and 1.9 µg/g fresh weight at 48 hours for sensitive cell line, and 1.7 µg/g fresh weight at 24 hours and 4.6 µg/g fresh weight at 48 hours for ETR-056 line, that is, the accumulation of protoporphyrin IX was observed. On the other hand, in ETR-245 and ETR-253 strain, little accumulation of protoporphyrin IX was recognized.

B. Cross-Resistance of a Cell Lines Tolerant to Photobleaching Herbicide Against Various Herbicides Further, cross-resistance of a resistant strain tolerant to herbicides with various modes of action was examined. Sensitivity to fomesafen (trade mark: FLEX) and oxadiazon (trade mark: RONSTAR), which are photobleaching herbicide and accumulate protoporphyrin IX; pyrazoxyfen (trademark: PAICER) which is a chlorophyll synthesis inhibitor and causes bleaching; DPX-84 and bialaphos (trademark: BASTA) and glyphosate (trademark: ROUNDUP) which are an inhibitor of the amino acid synthesis; butachlor (trademark: MACHETE) which is a protein synthesis inhibitor; propanil (trademark: STAM) which is an inhibitor of light synthesis photochemical system II and paraquat (trademark: PREEGLOX) which is an inhibitor of photosystem I and produces an active oxygen was compared. Into MS agar medium containing each herbicides, each resistant strain was transplanted and minimum inhibition concentration (MIC) was measured. As a result (Table 3), each resistant cell line showed strong resistance to fomesafen and oxadiazon which are an inhibitor of protoporphyrinogen oxidase inhibitor and accumulate protoporphyrin IX. Further, ETR-056 showed resistance to paraquat, and ETR-253 showed resistance to pyrazoxyfen, DPX-84 and glyphosate. From the above results, ETR-056 was thought to have resistance to an active oxygen caused by overproduction of superoxide dismutase, and ETR-253 was thought to have resistance to many herbicides caused by decreasing of a membrane permeability, and ETR-245 was thought to have resistance caused by mutation of a target enzyme or overproduction of a target enzyme.

TABLE 3

Sensitivity of photobleaching herbicide resistant celllines to various herbicides

| | MIC (ppm) | | | |
|---|---|---|---|---|
| Herbicide | Sensitive strain | ETR-056 | ETR-245 | ETR-253 |
| fomesafen | 0.4 | 4 | 4 | 4 |
| oxadiazon | 1 | 1000 | 1000 | 1000 |
| butachlor | 100 | 100 | 100 | 100 |
| pyrazoxyfen | 100 | 100 | 100 | 200 |
| propanil | 100 | 100 | 100 | 100 |
| bialaphos | 10 | 1 | 1 | 10 |
| DPX-84 | 0.01 | 0.01 | 0.01 | 0.1 |
| glyphosate | 230 | 230 | 230 | 1000 |
| paraquat | 10 | 100 | 10 | 10 |

C. Sensitivity of Photobleaching Herbicide Resistant Cell Lines to the Other Et Herbicides MIC of compound A to the sensitive cell lines, ETR-056, ETR-245 and ETR-253 were measured. As the result, MIC to the sensitive cell line was 5 nM, but, MIC to the resistant cell lines were over 2,400 nM, and becomes apparent that the resistant cell lines have strong resistance to the compound A. Therefore, in the following examples, the compound A was used as a photobleaching herbicide and ETR-245 was used as a resistant strain.

D. Extraction of Crude Enzyme Preparation from Sensitive Cell and ETR-245 Cell Line Using the same procedures described in Nicolaus, B. et al. (1993) in *"Target Assay for Modern Herbicide and Related Phytotoxic Compound"* Lewis Publishers, pp. 35–41, five volume of extraction buffer (50 mM Tris-HCl (pH 7.5), 0.5 M sucrose, 0.2% BSA, 1 mM EDTA) was added to callus which was cultured in MS solid medium for one month, and homogenized. After filtration with gauze, filtrate was centrifuged with 10,000×g at 4° C. for 5 minutes. Thus obtained precipitate was suspended with 25 ml of ethanol buffer, centrifuged with 150×g at 4° C. for 2 minutes. Thus obtained supernatant was centrifuged with 4,000×g at 4° C. for 15 minutes, and the precipitate was dissolved with 2 ml of 20% glycerol. The protein amount in the obtained crude enzyme preparation was measured with the protein measuring kit (manufactured by Bio-Rad Co., Ltd.).

E. Preparation of Protoporphyrinogen IX

The powder of sodium amalgam was prpared as follows. Into a round flask of 500 ml volume, 13 g of mercury and 0.5 g of thin-layer metal sodium were added, and equilibrated with nitrogen gas for 5 minutes, and it was shaked for 5 minutesthen. 8.4 g of protoporphyrin IX was dissolved into 10 mM KOH containing 15 ml of 20% ethanol, incubated at 4° C. To 4 ml of the protoporphyrin IX solution, equal amount of reaction mixture (0.1 M MES, 50 mM ascorbic acid) was added, and 16 mg of sodium amalgam freshly prepared was added, and shaken vigorously under nitrogen gas in a dark. The reaction mixture was filtered with a three-layer glass filter in a dark, and diluted 2.5 times with 0.1 M MES (pH4.5), and divided into 1 ml each in a light-shielded test tube and stored at −80° C.

F. Measurements of Protoporphyrinogen Oxidase Activity 3 ml of reaction buffer (100 mM Tris-HCl (pH 7.6), 1 mM EDTA, 5 mM DTT, 0.03% Tween 80) were added to a cell of a fluorescence spectrophotometer, then, the crude enzyme prparation was added at the final concentration of 0.1 mg protein/ml, and it was heated gradually to room temperature. After heating, protoporphyrinogen IX was added at the final concentration of 2 $\mu$M, and the gaseous phase was replaced with nitrogen gas, and a reaction was started. Fluorescence was monitored with a spectrophotometer for 30 minutes starting 10 minutes after the start of the reaction, and enzyme activity was measured (Ex:405 nm,Em:631.5 nm).

G. Inhibitory Effect of Compound a on Protoporphyrinogen Oxidase Preparation Extracted from Etr-245 Cell Activity of protoporphyrinogen oxidase in crude enzyme preparation which was extracted from a sensitive tobacco and ETR-245 and the extent of inhibition by compound A were compared (Table 4). As a result, activity of the crude enzyme preparation derived from the sensitive strain was 2.39 units, and the activity of the crude enzyme liquid derived from ETR-245 strain was 2.85 units, and there was no large difference between the activities. On the other hand, 50% inhibition concentration ($IC_{50}$) value of compound A to the activity of protoporphyrinogen oxidase extracted from the sensitive cell line was 48 nM, on the other hand, $IC_{50}$ value of compound A to the enzyme activity extracted from ETR-245 was 5,000 nM, which showed the resistance of more than 100 times at enzyme level. Incidentally, since the reaction mixture became turbidat the concentration of more than 5,000 nM, it was impossible to measure the fluorescence. From the above results, the resistant mechanism in ETR-245 to the photobleaching herbicide could be thought that the some mutations in the structure of the enzyme occurred, and was not over production of protoporphyrinogen oxidase which was a target enzyme of photobleaching herbicide.

TABLE 4

Inhibitory effect of compound A on the protoporphyrinogen oxidase activity from sensitive and ETR-245 cell line

| Concentration of | Enzyme activity(unit) | |
| --- | --- | --- |
| Compound A (nM) | Sensitive | ETR-245 |
| 0 | 2.39 | 2.85 |
| 10 | 4.32 | 3.59 |
| 20 | 3.62 | — |
| 40 | 1.84 | 4.41 |
| 100 | 0.00 | 2.21 |
| 500 | 0.00 | 3.49 |
| 1,000 | 0.00 | 2.85 |

TABLE 4-continued

Inhibitory effect of compound A on the protoporphyrinogen oxidase activity from sensitive and ETR-245 cell line

| Concentration of | Enzyme activity(unit) | |
| --- | --- | --- |
| Compound A (nM) | Sensitive | ETR-245 |
| 2,400 | 0.00 | 2.48 |
| 5,000 | 0.00 | 1.56 |
| $IC_{50}$value(nM) | 48 | >5000 |

1 unit = 1 nM protoporphyrin IX/min/mg protein

Example 3

Cloning of Tobacco Protoporphyrinogen Oxidase cDNA

A. Preparation of mRNA 9 g of a green leaf of tobacco (Nicotiana tabacum CV. SR1) was cut, and it was homogenized in liquid nitrogen. To the homogenate, 40 ml of RNA extraction buffer (200 mM Tris-HCl (pH9.0), 100 mM NaCl, 10 mM EDTA, 0.5% SDS, 0.1% 2-ME) and 40 ml of Tris-saturated phenol were added, and shaken vigorously for 10 minutes, then centrifuged with 2,000×g for 10 minutes, and the supernatant was recovered. To the supernatant, equal amount of Tris-saturated phenol was added, and shaking for 10 minutes and centrifugation for 10 minutes were repeated. To the supernatant thus derived, equal amount of phenol: chloroform: isoamylalcohol (25:24:1) were added, and shaking for 10 minutes and centrifugation for 10 minutes were further repeated two times. To the supernatant thus derived, equal amount of chloroform: isoamylalcohol (24:1) were added, and shaking for 10 minutes and centrifugation for 3 minutes were conducted two times. To the supernatant thus derived, 1/10 amount of 3 M sodium citric acid (pH5.2) and 2.5 fold volume of ethanol were added, incubated for 30 minutes at −80° C. Then, after centrifugation at 2,000×g for 20 minutes at 4° C., the precipitate was washed with 70% ethanol. To the dried precipitation, distilled water was added at the final concentration of 1 mg/ml, and 10 M lithium chloride was added at the final concentration of 2 M. Fter incubation on ice for 2 hours, the precipitate was recovered with 2,000×g 30 minutes at 4° C., and total RNA fraction was obtained.

Purification of mRNA from the total RNA fraction was conducted by using origo dT span column (manufactured by Pharmacia), according to the attached manual.

B. Preparation of cDNA Library

Preparation of cDNA library was conducted by using SUPERSCRIPT LAMBDA SYSTEM cDNA library construction kit (manufactured by GIBCO BRL Co., Ltd.). By using this kit, cDNA can be inserted at the positive orientation against lacZ promoter of λgt22A, by using a primer-adaptor at the first strand synthesis.

4 $\mu$g of mRNA was used as a template for cDNA synthesis. cDNA first strand synthesis, cDNA second strand synthesis, ligation of adaptor, restriction enzyme digestion and column chromatography were conducted according to the attached manual. cDNA thus obtained was ligated with λgt22A, and phage particle was reconstructed using GIGA-PACK GOLD packaging kit (manufactured by Stragene Co., Ltd.), according to the attached manual. The primary library containing about one million and nine hundred thousand of independent clones were infected with E. coliY1090 (r−) strain, multiplies and stored as an amplification library.

C. Genetic Complementation

Using an *E. coli* SASX38 strain having deletion of hemG (protoporphyrinogen oxidase) gene, and by using the method of Nishimura (Nishimura, K. et al. (1995) *J. Biol. Chem.* 270:8076–8080), genetic complementation was conducted. To the SASX38 strain which had been pre-cultured in LB liquid medium containing 10 mM MgSO4 and $O_2$% maltose, the above-mentioned amplification library was infected and spread on LB solid medium, then gene expression was induced. After it was cultured for two days at 37° C., some large colonies with recovered growth were observed, among many small colonies. The large colony was cultured in LB liquid medium over night, then, chloroform was added at the final concentration of 4%, mixed sufficiently, incubated over 30 minutes at room temperature and centrifuged to obtain phage particles as supernatant. The phage particles thus obtained were again infected to *E. coli* Y1090(r−) stain, and a single plaque was suspended in SM medium containing 4% chloroform. The recombinant phage particle recovered was infected again to the SASX38 strain, and the phage which conferred restoration of poor growth of the *E. coli* was reselected. The expression of protoporphyrinogen oxidase activity in *E. coli* by these recombinant phage vector was confirmed by the above-mentioned method.

D. Analysis of cDNA Insert

Amplification of cDNA insert was conducted by PCR. That is, using total DNA in the recovered recombinant phage particle as a template, Taq DNA polymerase (TAKARA EX Taq, manufactured by Takara Shuzo Co., Ltd.), a forward primer (5'ATT GGT GGC GAC GAC TCC TGG AG-3', SEQ ID No. 4) and a reverse primer (5'-CCA GAC CAA CTG GTA ATG GTA GCG-3', SEQ ID No. 5) for λgt22A, 30 cycles of PCR were conducted in which one cycle comprises 94° C. for 1.5 minutes, 69° C. for 1.5 minutes and 72° C. for 2 minutes. A part of reaction product was analysed by agarose gel electrophoresis, and it became clear that around 2.0 kbp cDNA was amplified in all samples. The amplified cDNA was recovered by chloroform treatment and ethanol precipitation, then compared by a restriction enzyme digestion analysis, indicating that EcoRV site was observed in each cDNA.

E. Subcloning of cDNA Insert and Confirmation of Biological Activity

The largest cDNA insert among cDNA inserts amplified by PCR was inserted at the positive orientation against the lacZ promoter into EcoRV site of pBluescript SK(−), by using TA cloning method described in the above mentioned literatures (for example, *Current Protocols in Molecular Biology*, John Wiley & sons, Ausubel, M. et al.). That is, the pBluescript SK (−) was digested by EcoRV and recovered, and Taq DNA polymerase (TAKARA EX Taq, manufactured by Takara Shuzo Co., Ltd.) was added and reacted at 75° C. for 2 hours in the presence of dTTP to add T to 3' end of the plasmid DNA. After the addition of T, the plasmid recovered and the largest cDNA insert recovered after PCR were ligated using DNA Ligation Kit (manufactured by Takara Shuzo Co., Ltd.), according to the attached explanation. With thus obtained reaction mixture, competent cells of XL-1 Blue strain (manufactured by Stratagene Co., Ltd.) produced by the $CaCl_2$ method was transformed and spread on LB agar medium containing IPTG and ampicillin, and cultured at 37° C. for overnight. After the incubation, some white colonies with cDNA insert were selected, and cultured in LB liquid medium containing ampicillin for overnight, then plasmid DNA was prepared by the alkaline lysis method. Thus obtained plasmid DNA was digested with a restriction enzyme, and *E. coli* having a plasmid in which cDNA was inserted at the positive orientation of the promotor, was selected. Thus obtained plasmid was named as pBNtPX-1 (FIG. 1), and glycerol was added at the final concentration of 15% to the *E. coli* culture medium and stored at −80° C.

The *E. coli* having pBNtPX-1 was cultured in LB liquid medium containing ampicillin for overnight, then the plasmid was purified in large quantity by the Cesium chloride method. Using the obtained plasmid, the competent cell of *E. coli* SAX38 strain produced by the $CaCl_2$ method was transformed. The transformed SASX38 strain was spread on LB agar medium, and cultured for overnight at 28° C. As a result, in case that pBNtPX-1 was used, many large colonies with recovered growth were observed among small colonies. As described in the above, protoporphyrinogen oxidase activity in *E. coli* by pBNtPX-1 was confirmed.

F. Analysis of Nucleotide Sequence of cDNA

From the pBNtPX-1 which recovered the poor growth of *E. coli* SASX38 strain, deletion clones were produced by using Deletion Kit for Kilo-Sequence (manufactured by Takara Shuzo Co., Ltd.), according to the attached manual, and the nucleotide sequence and amino acid sequence in the open reading frame were analyzed by using Cycle Sequencing Kit AMPLITAO-FS (manufactured by Perkin-Elmer Corporation) and an auto sequencer (manufactured by ABI PRISM 310, Perkin-Elmer Corporation) according to the attached manual. The obtained nucleotide sequence and the amino acid sequence in the open reading frame are shown in the SEQ ID No. 1. By using GENETYX (SDC Co., Ltd.), gene analysis software, nucleotide sequence and amino acid sequence were compared with those of the protoporphyrinogen oxidase of *Arabidopsis thaliana* which have already reported (WO 95/34659), and the homology was examined. As a result, pBNtPX-1 showed high homology of 69% at nucleotide level and 76% at amino acid level with the chloroplast-type protoporphyrinogen oxidase cDNA of *Arabidopsis thaliana*, and considered to be a chloroplast-type protoporphyrinogen oxidase cDNA of tobacco.

Further, the polypeptide was confirmed to be the protoporphyrinogen oxidase, from the fact that it has a dinucleotide binding domain (GXGXXG) (Nishimura, K. et al. (1995) *J. Biol. Chem.* 270:8076–8080), which is conserved in the N-terminal of protoporphyrinogen oxidase of many organisms. Further, in protoporphyrinogen oxidase of *B. subtilis* and animal, only from 8 to 11 amino acids were found at up-stream of the domain, on the contrary, 77 amino acids were found in a chloroplast-type protoporphyrinogen oxidase gene of tobacco.

Table 5 Comparison of amino acid sequence of tobacco (SEQ. ID. NO. 2) (upper column) and *Arabidopsis thaliana* (SEQ. ID. NO. 11) (lower column) of a chloroplast-type protoporphyrinoge oxidase.

```
Homology: 75.9%
    1' MTTTPIANHPNIFTHQSSSSPLAFLNRTSFIPFSSISKRN-SVN-CNGWRTRCSVAKDYT
             *...*...*.    ...*.**.*  ..*  ..  * *****  .  *
    1"                           MELSLLRPTTQSLLPSFSKPNLRLNVYKPLRLRCSVAGGPT 59' VPSSAVDGGPAAEL--DCVIVGAGISGLCIAQVMSANY----PNLMVTEARDRAGGNITT
        *    ..  ....  ***.*****.......    *.**..*****.*
```

-continued

```
 42"  VGSSKIEGGGGTTITTDCVIVGGGISGLCIAQALATKHPDAAPNLIVTEAKDRVGGNIIT

113'  VERDGYLWEEGPNSFQPSDPMLTMAVDCGLKDDLVLGDPNAPRFVLWKGKLRPVPSKLTD
      * .*..******************.**.***********.*******.************
102"  REENGFLWEEGPNSFQPSDPMLTMVVDSGLKDDLVLGDPTAPRFVLWNGKLRPVPSKLTD

173'  LPFFDLMSIPGKLRAGFGAIGLRPSPPGHEESVEQFVRRNLGGEVFERLIEPFCSGVYAG
      *********.**.******.*.******.*****.*******.****************
162"  LPFFDLMSIGGKIRAGFGALGIRPSPPGREESVEEFVRRNLGDEVFERLIEPFCSGVYAG

233'  DPSKLSMKAAFGKVWKLEETGGSIIGGTFKAIKERSSTPKAPRDPRLPKPKGQTVGSFRK
      *****************..***********.**...***.*******.*.*********
222"  DPSKLSMKAAFGKVWKLEQNGGSIIGGTFKAIQERKNAPKAERDPRLPKPQGQTVGSFRK

293'  GLRMLPDAISARLGSKLKLSWKLSSITKSEKGGYHLTYETPEGVVSLQSRSIVMTVPSYV
      ******.********.*******.***.*.***.******.*.**.**.*.******.*
282"  GLRMLPEAISARLGSKVKLSWKLSGITKLESGGYNLTYETPDGLVSVQSKSVVMTVPSHV

353'  ASNILRPLSVAAADALSNFYYPPVGAVTISYPQEAIRDERLVDGELKGFGQLHPRTQGVE
      **..*****..**.***..******.**.****.****.* *.****************
342"  ASGLLRPLSESAANALSKLYYPPVAAVSISYPKEAIRTECLIDGELKGFGQLHPRTQGVE

413'  TLGTIYSSSLFPNRAPKGRVLLLNYIGGAKNPEILSKTESQLVEVVDRDLRKMLIKPKAQ
      ***************.**.********...*..****.*...***.************..
402"  TLGTIYSSSLFPNRAPPGRILLLNYIGGSTNTGILSKSEGELVEAVDRDLRKMLIKPNST

473'  DPLVVGVRVWPQAIPQFLVGHLDTLSTAKAAMNDNGLEGLFLGGNYVSGVALGRCVEGAY
      ***  .****************.*.*.***......* ***********.*********** 
462"  DPLKLGVRVWPQAIPQFLVGHFDILDTAKSSLTSSGYEGLFLGGNYVAGVALGRCVEGAY

533'  EVASEVTGFLSRYAYK   548
      *.* **..*.******
522"  ETAIEVNNFMSRYAYK   537
```

Example 5

Figure 2:
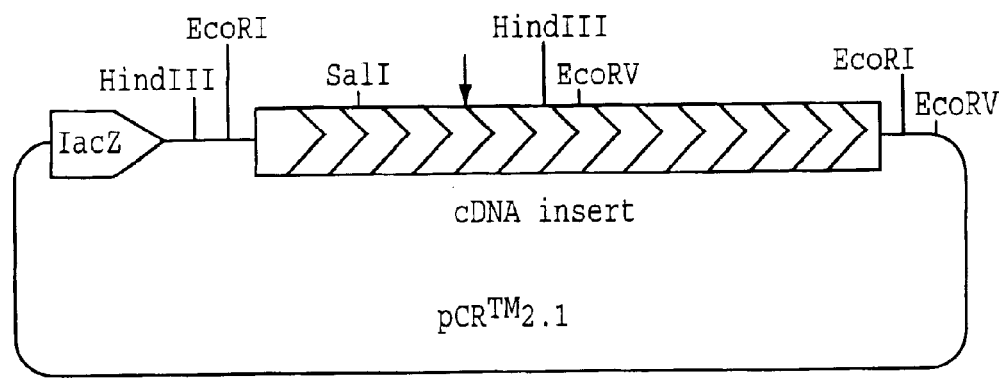
FIG. 2 is schematic figure of pCR-HC and pCR-RC ▼:mutation in pCR-RC c is mutated to T at 717th nucleotide in SEQ ID No.1, and alanine is mutated to valine at 231th amino acid)

Protoporphyrinogen Oxidase cDNA of Tobacco Callus Tolerant to Photobleaching Herbicide A. Cloning by PCR After extracting the total RNA by the SDS/phenol method from photobleaching herbicide tolerant callus, ETR-245 cell line, and sensitive cell line, respectively, mRNA was purified by mRNA purification Kit (manufactured by Pharmacia Co., Ltd.). Reverse transcription reaction was conducted using 1 μg of the purified mRNA as a template and using Oligo(dT) 12-18 (manufactured by Life Technology Oriental Inc.) as a primer and using SUPERSCRIPT™ RNaseH-Reverse Transcriptase (manufactured by Life Technology Oriental Inc.) according to the attached manual at 37° C. for 1 hour, and then cDNA was purified by phenol/chloroform extraction and ethanol precipitation. Protoporphyrinogen oxidase cDNA was attempted to be amplified by PCR, using the obtained cDNA as a template. A forward primer (5'-GCG GTC TAC AAG TCA GGC AGT CAT-3', SEQ ID No.6) and a reverse primer(5'-CAT GCC AAT TTT CCC AAG GCA TGA TCG TAT T-3', SEQ ID No.7) were used as the primer for PCR. One cycle of 94° C. for 3 minutes, and 30 cycles of 94° C. for 20 seconds, 61° C. for 30 seconds and 72° C. for 1 minute and 30 seconds and one cycle of 72° C. for 5 minutes were conducted by using a Taq DNA polymerase (manufactured by TAKARA EX Taq, Takara Shuzo Co., Ltd.) in a thin wall tube. A part of the obtained PCR reaction mixture was analyzed by agarose gel electrophoresis, DNA fragment having about 1.7 kbp was observed. These can be thought to be protoporphyrinogen oxidase cDNA fragment. Accordingly, these DNA was ligated with the plasmid vector pCRT™2.1 having T over hang, using Original TA CLONING kit (manufactured by Invitrogene Co., Ltd.), according to the attached manual. And, with a ligation mixture, the competent cell of E. coli, XL-1 Blue strain (manufactured by Stratagene Co., Ltd.) prepared by the $CaCl_2$ method, was transformed, and spread on LB agar medium containing IPTG, Xgal and ampicillin, and incubated at 37° C. for overnight. After the incubation, some white colonies with cDNA insert were selected, cultured with shaking in LB liquid medium containing ampicillin for overnight, then plasmid DNA was prepared by the alkaline lysis method. The obtained plasmid DNA was digested with restriction enzyme, and E. coli having a plasmid in which each cDNA was inserted at the positive orientation against the promotor was selected. Plasmids in which chlorophyll type protoporphyrinogen oxidase cDNA were inserted were named as PCR-HC or pCR-RC (FIG. 2), respectively. Then, glycerol was added to the final concentration of 15%, and the E. coli was stored at −80° C.

The E. coli having each of these two kind of plasmid were cultured in LB liquid medium containing ampicillin for overnight, then large quantity of plasmid wsa purified by the Cesium chloride method. Competent cells of E. coli SASX38 strain produced by the $CaCl_2$ method was transformed with the obtained plasmid. The transformed SASX38 strain was spread on LB agar medium and incubated at 28° C. for overnight. As a result, in any case that any incubated plasmid was used, many large colonies whose growth was recovered were observed among small colonies. As described, expression of the protoporphyrinogen oxidase activity in E. coli by pCR-HC and pCR-RC was confirmed.

B. Comparison of Resistance of Each Gene Product to Compound a

The E. coli SASX38 strain containing either of the above-described two kinds of plasmid was cultured with shaking in LB liquid medium containing 50 μg/ml of ampicillin at 28° C. for overnight. After measuring of $OD_{600}$ value, the culture was added into the LB liquid medium containing 50 μg/ml of ampicillin and 0, 1, 10, 100, 1000, 2,000, 5,000 or 10,000 nM of compound A, so as to become same $OD_{600}$ value, and were cultured with shaking at 28° C. A part was collected periodically, $OD_{530}$ value were measured by a micro plate reader (MTP-120, manufactured by Corona Electric Co., Ltd.), and the concentration at which the growth of *E. coli* of control (Compound A 0 nM) was inhibited by 50% ($IC_{50}$) was calculated. As a result, the $IC_{50}$ value in the *E. coli* containing pCR-HC or PCR-RC was about 2.5 nM or 10,000 nM or more, respectively and R/S ratio ($IC_{50}$ value of a resistant type/$IC_{50}$ value in a wild type) was over 4,000. Incidentally, since the medium became turbid at the concentration of 10,000 mM or more, it was impossible to measure $OD_{530}$ value. From the above result, the resistant mechanism to Compound A of protoporphyrinogen oxidase in ETR-245 was thought that some mutation occurred in chloroplast-type protoporphyrinogen oxidase gene, and the enzyme was converted to a photobleaching herbicide resistant type.

C. Comparison of the Nucleotide Sequence of the Chloroplast Type Protoporphyrinogen Oxidase cDNA Comparison of the entire nucleotide sequence of the protoporphyrinogen oxidase cDNA derived from the sensitive and ETR-245 cell line, contained in pCR-HC or pCR-RC, respectively was performed. From the nucleotide sequence information of the cDNA derived from tobacco leaf, a primer set for primer-walking was synthesized, and entire nucleotide sequence of the both cDNA was compared. As a result, the nucleotide sequence of pCR-HC was quite the same sequence as that of protoporphyrinogen oxidase cDNA derived from the tobacco leaf, but, in the pCR-RC, a mutation was observed in only one point. That is, C was mutated to T at 717th nucleotide in SEQ ID No. 1, as the result, alanine was mutated to valine at 231th amino acid in SEQ ID No.1. Amino acid sequence of the protoporphyrinogen oxidase resistant to the photobleaching herbicide is shown in SEQ ID No. 2, and the nucleotide sequence of the cDNA is shown in SEQ ID No.3. The homology of tobacco and *Arabidopsis thaliana* protoporphyrinogen oxidase amino acid sequence was high (Table 5), this mutation was almost the same mutation as in the mutation to the photobleaching herbicide resistant type (pArac-lVal), accompanied by the mutation from alanine of 220th amino acid to valine in *Arabidopsis thaliana* protoporphyrinogen oxidase, described in Wo/95/34659.

Example 6

Photobleaching Herbicide Resistant Type cDNA of *Arabidopsis thaliana*

Figure 3:
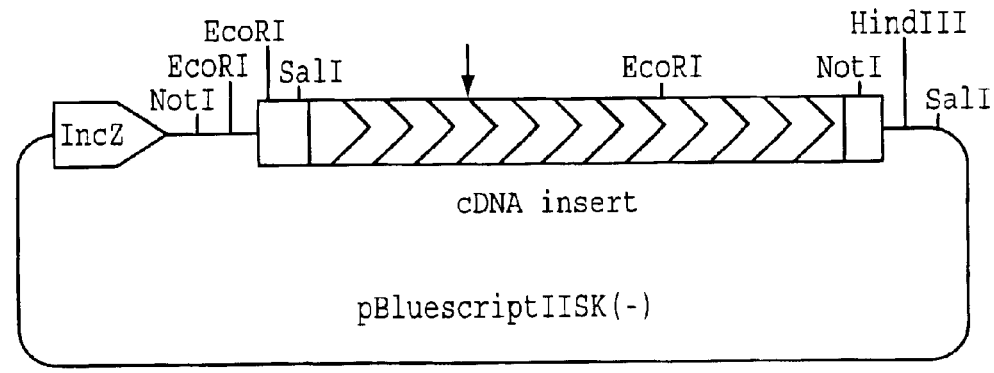
FIG. 3 is schematic figure of pBAtPX-C and pBAt-RC ▼:mutation in pBAtPX-RC (same mutation as pAraC-1Val in WO 95/34659)

A. Cloning of Chloroplast-Type Protoporphyrinogen Oxidase cDNA of *Arabidopsis thaliana* and Conversion to the Photobleaching Herbicide Resistant Type The cloning of chloroplast-type protoporphyrinogen oxidase gene was conducted by preparing cDNA library and genetic complementation method in which *E. coli* mutant strain SAS38 defective HemG, similarly in the case of tobacco. Sub-cloning of the cDNA thus obtained to EcoRV site of pBluescript SK(-) was conducted by using the TA coning method. A plasmid showing a bioactivity in which the protoporphyrinogen oxidase gene was inserted at the positive orientation against the promotor was named as pBAtPX-C (FIG. 3). The entire nucleotide sequence of the plasmid was confirmed to be entirely the same as the known sequence (W/O 95/34659), by the primer walking using a primer designed from the sequence.

This plasmid was used for the production of a protoporphyrinogen oxidase cDNA resistant to photobleaching herbicide, by the mutation of cDNA valine from alanine at 220th amino acid, as described in WO 95/34659. Single strand DNA was prepared from *E. coli* XL-1 Blue containing pBAtPX—C by using a helper phage VCS-M13 (manufactured by Stratagene Co., Ltd.). Then, using a kit for site-specific mutagenesis (manufactured by Mutan-K, Takara Shuzo Co., Ltd.) in which the Kunkel method was utilized and oligonucleotide for the introduction (5'-GGT GTT TAT GTT GGT GAT CC-3') (SEQ ID No. 8), the cDNA was converted to photobleaching herbicide resistant type. In order to avoid non-specific mutation in the course of site-specific mutagenesis, resubcloning of the cDNA in the plasmid thus obtained into pBluescript SK(-) was again conducted. Further, the entire nucleotide sequence of the cDNA was determined and it was confirmed to be the objective nucleotide sequence. The final plasmid which was tolerant to the light requiring herbicide was named as pBAtPX—RC (FIG. 3).

B. Comparison of Resistance to Compound a of Two Type of Protoporphyrinogen Oxidase from *Arabidopsis Thaliana*

Comparison of the resistance to the Compound A of wild type protoporphyrinogen oxidase gene product encoded by pBAtPX-C and resistant type gene product encoded by pBAtPX-RC was attempted. Using the same method as described in the comparison of resistance to the Compound A of each gene product in Example 5B, $IC_{50}$ value of each protoporphyrinogen oxidase to the Compound A was measured, respectively. As the result, $IC_{50}$ value was about 5 nM in case of the wild type, and 1,500 nM in the resistant type, and R/S ratio ($IC_{50}$ value of the resistant type/$IC_{50}$ value of the wild type) was about 300. R/S ratio in the case of tobacco was over 4,000, therefore, the R/S ratio in the case of tobacco was found to be over ten times higher, comparing with the *Arabidopsis thaliana*. This difference was highly unexpected result, when the high homology of the amino acid sequence between both protoporphyrinogen oxidase was taken into consideration.

Example 7

Resistance to Several Compounds

By using the *E. coli* SASX38 strain having pCR-HC with tobacco wild type protoporphyrinogen oxidase cDNA, the *E. coli* SASX38 strain having pCR-RC with tobacco resistant type protoporphyrinogen oxidase gene, the *E. coli* SASX38 strain having pBAtPX-C with *Arabidopsis thaliana* wild type protoporphyrinogen oxidase gene and the *E. coli* SASX38 strain having pBAtPX-RC with *Arabidopsis thaliana* resistant type protoporphyrinogen oxidase cDNA, $IC_{50}$ value of several pyrazole compound (Compound B, C, D, E, F and G) to the growth of each *E. coli* was measured, and R/S ratio ($IC_{50}$ values of the resistant type/$IC_{50}$ value of the wild type) in the *Arabidopsis thaliana* cDNA and R/S ratio in tobacco cDNA was compared. As the result(Table 6), the R/S ration in tobacco cDNA was found to be over ten times higher, comparing with the R/S ratio in the *Arabidopsis thaliana* gene. This difference was highly unexpected, when the high homology of the amino acid sequence between both protoporphyrinogen oxidase was taken into consideration.

TABLE 6

Resistance to Compound A analogous (*E. coli* liquid culture method with shaking)

| | $I_{50}$ (nM) | | | | | |
|---|---|---|---|---|---|---|
| | Arabidopsis thaliana | | | Tobacco | | |
| Compound | Wild | Resistant | R/S[a] | Wild | Resistant | R/S[b] | Superiority c) |
| Comp.B | 21 | 18,000 | 860 | 2.2 | >20,000 | 9,100 | >10.6 |
| Comp.C | 3.0 | 1,800 | 600 | 0.25 | 2,200 | 8,800 | 14.7 |
| Comp.D | 0.14 | 280 | 2,000 | 0.027 | 670 | 25,000 | 12.5 |
| Comp.E | 4.2 | 4,000 | 950 | 0.52 | 6,300 | 12,000 | 12.6 |
| Comp.F | 23 | 6,400 | 280 | 3.2 | 15,000 | 4,700 | 16.8 |
| Comp.G | 19 | 8,700 | 460 | 3.1 | 17,000 | 5,500 | 12.0 |

[a,b] Resistant type/Wild type
c) b/a

Example 8

Resistance to Compound a in Transformed Plant
A. Construction of a Vector for Plant Transformation Wild type and resistant type protoporphyrinogen oxidase cDNA of Tobacco and *Arabidopsis thaliana* were inserted into T-DNA in binary vector pBI121 (manufactured by Clontech Co., Ltd.) used for GUS gene introduction. At first, pBI121 was digested with SacI, and made to be blunt end with T4DNA polymerase (manufactured by Takara Shuzo Co., Ltd.). The DNA fragment thus obtained was digested with BamHI, then, after separation to a GUS gene fragment and a plasmid fragment by agarose gel electrophoresis, the plasmid fragment was recovered. On the other hand, pCR-HC having tobacco wild type protoporphyrinogen oxidase cDNA, pCR-RC having tobacco resistant type protoporphyrinogen oxidase cDNA, pBAtPX-C having *Arabidopsis thaliana* wild type protoporphyrinogen oxidase cDNA and pBAtPX—RC having *Arabidopsis thaliana* resistant type protoporphyrinogen oxidase cDNA were digested with XhoI, respectively, then, made to be blunt end with a Klenow fragment of DNA polymerase I (manufactured by Takara Shuzo Co., Ltd.). The DNA fragment thus obtained was digested with BamHI, then, after separation to the protoporphyrinogen oxidase gene fragment and a plasmid fragment by the agarose gel electrophoresis, the protoporphyrinogen oxidase gene fragment was recovered.

The plasmid fragment derived from pBI121 and each protoporphyrinogen oxidase cDNA fragment were ligated using DNA Ligation Kit (manufactured by Takara Shuzo Co., Ltd), and *E. coli* was transformed and spread on LB agar medium containing kanamycin and incubated at 37° C. for overnight.

Figure 4:
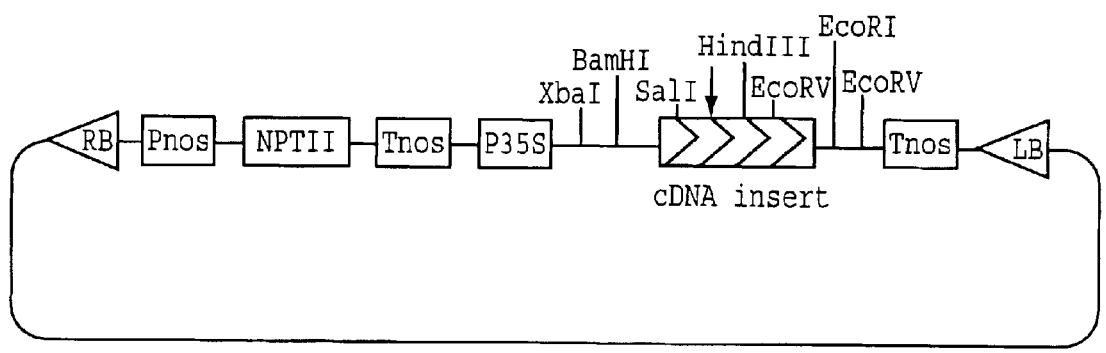
FIG. 4 is schematic figure of pBI-NtPX-HC and pBI-NtPX-RC ▼:mutation in pBI-NtPX-RC c is mutated to T at 717th nucleotide in SEQ ID No.1, and alanine is mutated to valine at 231th amino acid)
Figure 5:
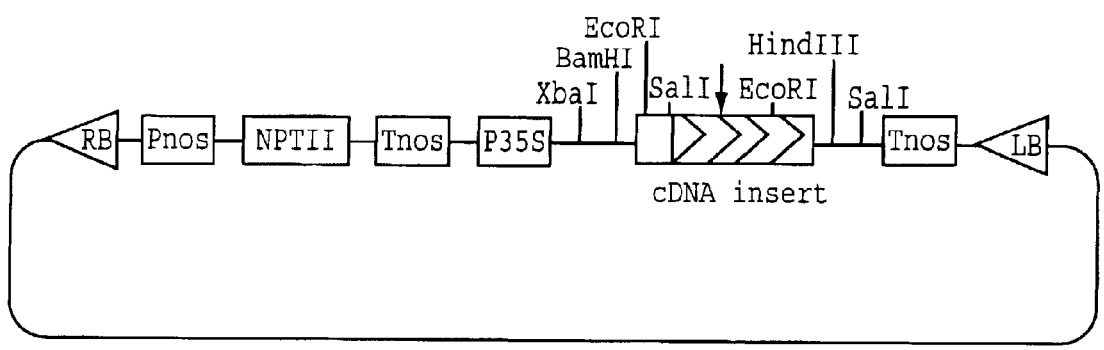
FIG. 5 is schematic figure of pBI-AtPX-HC and pBI-AtPX-RC ▼:mutation in pBI-AtPX-RC (same mutation as pAraC-1Val in WO 95/34659)

After the culture, some colonies which showed resistance to Kanamycin were selected, and cultured with shaking in LB liquid medium containing Kanamycin for overnight, then, plasmid DNA was prepared by the alkaline lysis method. The plasmid DNA was digested with restriction enzyme, and *E. coli* having a plasmid in which each protoporphyrinogen oxidase cDNA was inserted was selected. The binary vector in which tobacco wild or resistant type protoporphyrinogen oxidase gene was inserted were named as pBI-NtPX-HC or pBI-NtPX-RC (FIG. 4), respectively, and the binary vector in which *Arabidopsis thaliana* wild or resistant type protoporphyrinogen oxidase gene was inserted were named as pBI-AtPX-HC or pBI-AtPX-RC (FIG. 5), respectively, and glycerol was added at the final concentration of 15% to the *E. coli* culture and it was stored at −80° C.

B. Introduction of a Plant Transformation Vector into *Agrobacterium tumefaciens*

The four kinds of binary vector above-mentioned were introduced into *Agrobacterium* tumefacience LBA4404 strain (manufactured by Clontech Inc.), using the Triparental mating method. That is, *E. coli* HB101 strain having binary vector, *E. coli* HB101 strain (Clontech Inc.) having helper plasmid pRK2013 and *A. tumefacience* LBA4404 strain were cultured at 28° C. for two days in agar medium for bacterial culture, then the three strains were sufficiently mixed, and cultured at 28° C. for further two days. The mixture was streaked onto AB agar medium having kanamycine and streptomycin (0.3% $K_2HPO_4$, 0.1% $NaH_2PO_4$, 0.1% $NH_4Cl$, 0.03% $MgSO_4.7H_2O$, 0.5% glucose, 1.5% agar for bacterial culture). After four days at 28° C., single colony was picked up and incubated in AB medium containing kanamycin and streptomycin 28° C. for four days, then the plasmid was confirmed by the alkaline lysis method. To the *A. tumefacience* LBA4404 strain was added glycerin to become 15%, stored at −80° C.

C. Production of a Transformed Plant by *A. Tumefacience*

The *A. tumefacience* having the binary vector which had been stored at −80° C. was cultured with shaking at 27° C. for 24 hours in 523 liquid medium (1% sucrose, 0.8% Bacto-tryptone, 0.4% Bacto-yeast extract, 0.2% K2HPO4, 0.03% MgSO4.7H2O) containing kanamycin. A disk (9 mm diameter) of a tobacco (*N. Tabacum* var. *SR*1) leaf which had been surface sterilized was immersed for one minute into the culture of the *A. tumefacience*, and then the culture liquid attached thereon was removed with a sterilized paper towel. The leaf disk was transferred into MS agar medium containing 0.6% agar in which 2 ppm NAA and 0.2 ppm BA were added, with the reverse side of leaf being made upside, and incubated at 25° C. for 48 hours. The leaf disk was transferred into MS liquid medium containing 500 ppm carbenicillin, 200 ppm claforan, 2 ppm NAA and 0.2 ppm BA and cultured with shaking at 27° C. for 48–72 hours to remove *A. tumefacience*. The leaf disk was transferred into MS liquid medium containing 0.6% agar, 100 ppm of carbenycillin, 200 ppm of claforan and 150 ppm of kanamycin, 2 ppm NAA and 0.2 ppm BA and incubated at 27° C. for 2–3 weeks and formation of shoot was induced. The shoot was transferred into medium for root development (½ MS, 0.02 ppm IBA, 1.5% sucrose, 0.2% gellan gum) and development of root was introduced. The young plant thus obtained was transferred into culture soil, and was grown in a green house.

D. Confirmation of the Introduced Gene in the Transformed Plant

The introduced gene in the transformed plant was confirmed using the PCR method. That is, genomic DNA was extracted from the leaf of the transformed plant, and purified by the CTAB method. Using Taq DNA polymerase, a forward primer for CaMV 35 S promoter (5'-CAC AGA TGG TTA GAG AGG CTT ACG CAG-3', SEQ ID No.9), a reverse primer for NOS terminator (5'-TCA TCG CAA GAC CGG CAA CAG GAT TCA-3', SEQ ID No. 10), and using the obtained genome DNA as a template, and in a thin wall tube, one cycle of 94° C. 3 minutes, and 30 cycles of 94° C. 20 seconds, 62° C. 30 seconds and 72° C. 3 minutes were conducted. A part of the product was analyzed by agarose gel electrophoresis, approximately 2.7 kb DNA fragment was observed in more than 80% of the plant.

E. Examination for Resistance to Compound A

From the transformed plant with which the confirmation of introduction of gene was finished, and non-transformed plant used as a control, a leaf almost the same position of the leaf was picked and 9 mm diameter leaf disks were prepared, and floated on a dish in which 0, 125, 250, 1,250, 2,500, 5,000, 12,500 nM of compound A aqueous solution were contained. After incubation at 27° C. for one week under continuous strong light, the bleaching of the leaf disks was observed, and the permissive concentration to compound A was calculated. As a result (Table 7), in case that the tolerant type of protoporphirinogen oxidase cDNA from tobacco was introduced by pBI-NtPX-RC, more than 100 times of tolerance was observed comparing to the control non-transformed plant. However, in case that rsistant type cDNA from Arabidopsis thaliana was introduced by pBI-AtPX-RC, 4 times of resistance was observed comparing to the control, and in case that the wild type cDNA was introduced, high resistance was not observed in each case. Accordingly, it has now been found that in order to express tolerance to photobleaching herbicide, the tobacco tolerant type protoporphyrinogen oxidase cDNA of the present invention is useful.

TABLE 7

Resistance to compound A in the transformed tobacco plant level (the Leaf disk method)

| Introduced gene (Vector) | Permission conc. to compound A | Resistance |
| --- | --- | --- |
| None | 125 nM | X 1 |
| Arabidopsis thaliana Wild type (pBI-AtPX-HC) | 250 nM | X 2 |

TABLE 7-continued

Resistance to compound A in the transformed tobacco plant level (the Leaf disk method)

| Introduced gene (Vector) | Permission conc. to compound A | Resistance |
| --- | --- | --- |
| Arabidopsis thaliana resistant type (pBI-AtPX-RC) | 500 nM | X 4 |
| Tobacco Wild type (pBI-AtPX-HC) | 500 nM | X 4 |
| Tobacco resistant type (pBI-AtPX-RC) | >12,500 nM | >X 100 |

The present inventors have investigated in the protoporphyrinogen oxidase of a higher plant, and as the result, succeeded in the cloning and expression of the protoporphyrinogen oxidase gene tolerant to photobleaching herbicide, derived from tobacco. When tolerance of the present gene product to photobleaching herbicide was compared to that of protoporphyrinogen oxidase derived from Arabidopsis thaliana which has already been reported, it has now been found that the tolerance of the present gene product is far superior, in spite of the high homology in the structure of both gene.

INDUSTRIAL AVAILABILITY

Protoporphyrinogen oxidase which is new and tolerant to photobleaching herbicide has been obtained, thus, by expressing the enzyme in a host plant, production of a plant which is highly tolerant to light requiring herbicides is possible.

---

What is claimed is:

1. An isolated polypeptide comprising the amino acid sequence of SEQ ID NO:2.

* * * * *